(12) United States Patent
Low

(10) Patent No.: US 11,664,103 B2
(45) Date of Patent: May 30, 2023

(54) AUTHENTICATION METHODS AND SYSTEMS FOR DISPENSED PRESCRIPTIONS

(71) Applicant: Gordon K Low, Belmont, MA (US)

(72) Inventor: Gordon K Low, Belmont, MA (US)

( * ) Notice: Subject to any disclaimer, the term of this patent is extended or adjusted under 35 U.S.C. 154(b) by 471 days.

(21) Appl. No.: 16/790,864

(22) Filed: Feb. 14, 2020

(65) Prior Publication Data

US 2020/0265938 A1  Aug. 20, 2020

Related U.S. Application Data

(60) Provisional application No. 62/918,863, filed on Feb. 14, 2019.

(51) Int. Cl.
| | | |
|---|---|---|
| *G16H 20/13* | (2018.01) | |
| *G06K 7/10* | (2006.01) | |
| *G16H 10/60* | (2018.01) | |
| *G06F 16/9035* | (2019.01) | |

(52) U.S. Cl.
CPC ......... *G16H 20/13* (2018.01); *G06F 16/9035* (2019.01); *G06K 7/1097* (2013.01); *G16H 10/60* (2018.01)

(58) Field of Classification Search
CPC .... G16H 20/13; G16H 10/60; G06F 16/9035; G06K 7/1097
See application file for complete search history.

(56) References Cited

U.S. PATENT DOCUMENTS

| | | | |
|---|---|---|---|
| 9,189,728 B2 * | 11/2015 | Stuck | G06K 19/14 |
| 2007/0219916 A1* | 9/2007 | Lucas | G06Q 10/08 |
| | | | 705/58 |
| 2011/0186629 A1* | 8/2011 | Stuck | G06K 19/14 |
| | | | 235/380 |
| 2016/0292386 A1* | 10/2016 | Finkelstein | G16H 10/60 |
| 2020/0085694 A1* | 3/2020 | Patel | G08B 21/24 |

* cited by examiner

*Primary Examiner* — Michael Collins
(74) *Attorney, Agent, or Firm* — Ascentage Law, PLLC

(57) ABSTRACT

Methods and systems for providing authentication of dispensed prescriptions include utilizing one or more authenticator indicia, wherein the authenticator indicia have a plurality of indicia components including unique identification number for associating a dose of medication in a database. The authenticator indicia are configured on dose containers, such as blister packs and pill packs, to be scannable by a third-party scanning tool. The scanned information can be received by an authentication communication system to establish authenticity and other information such as adherence and compliance information related to the dispensed prescriptions.

7 Claims, 19 Drawing Sheets

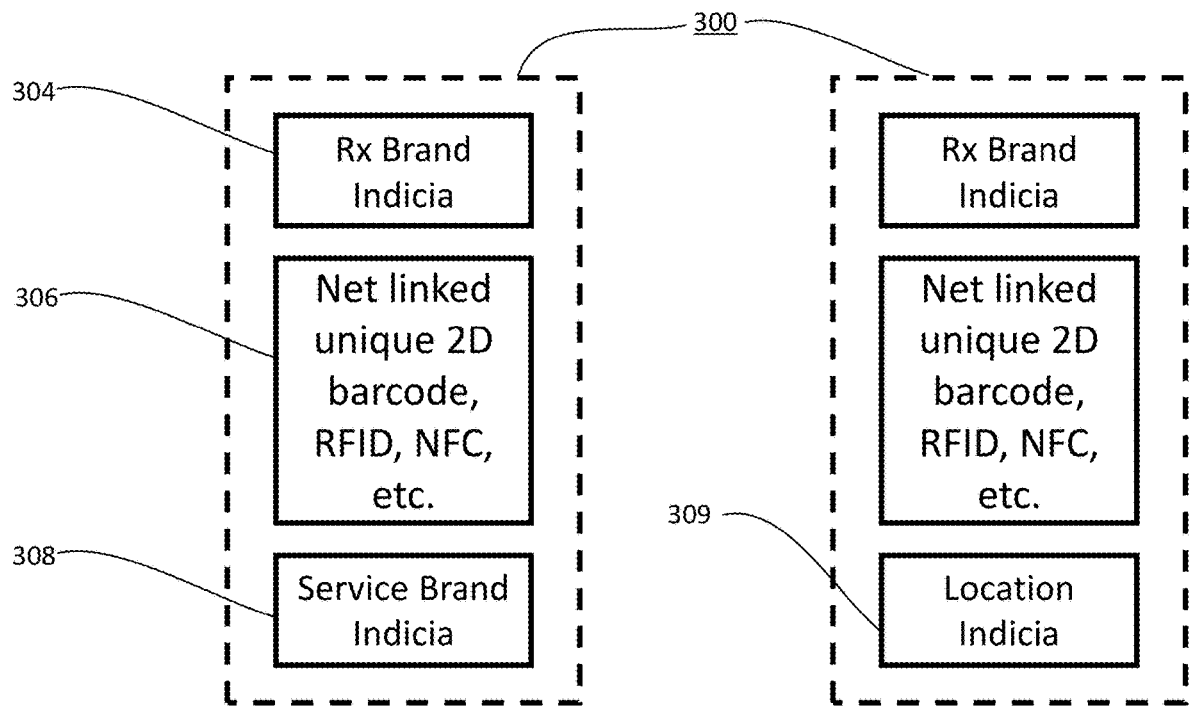
FIG. 3A.1          FIG. 3A.2
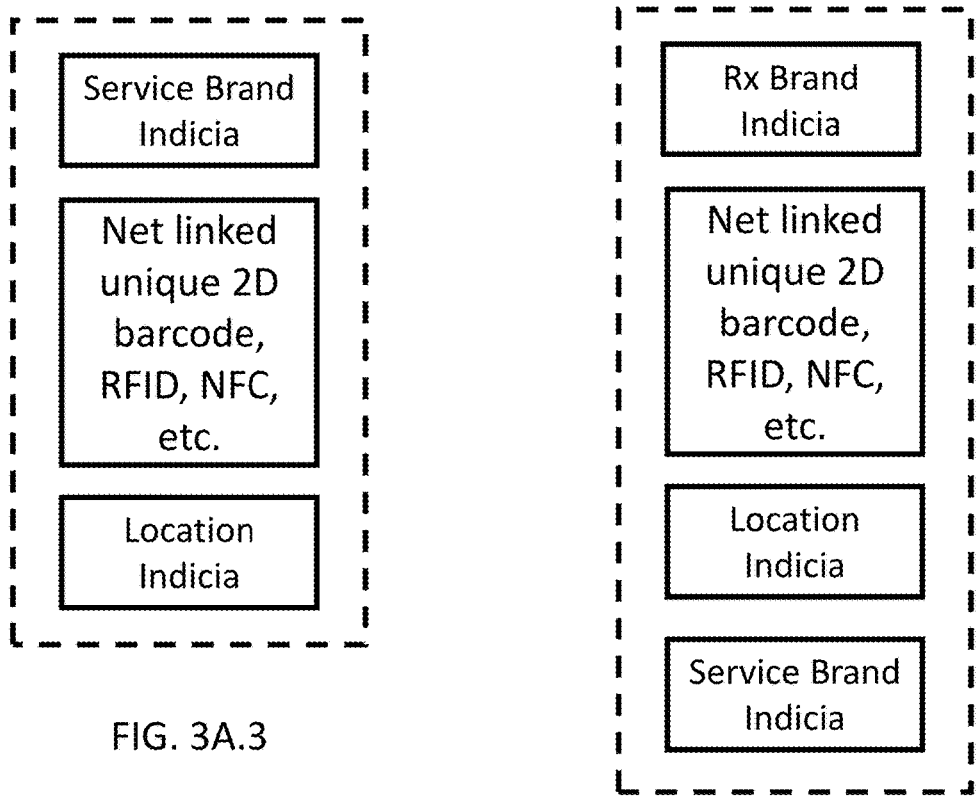
FIG. 3A.3          FIG. 3A.4

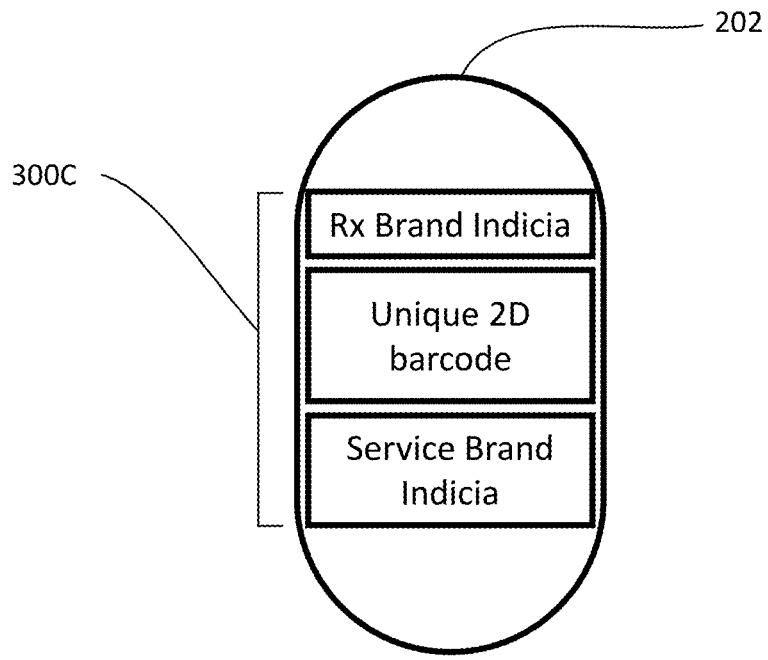
FIG. 3D.1
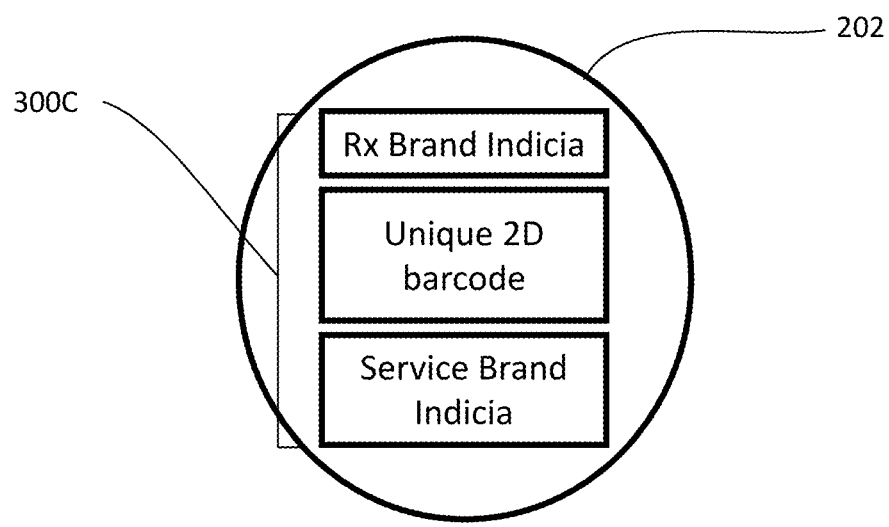
FIG. 3D.2

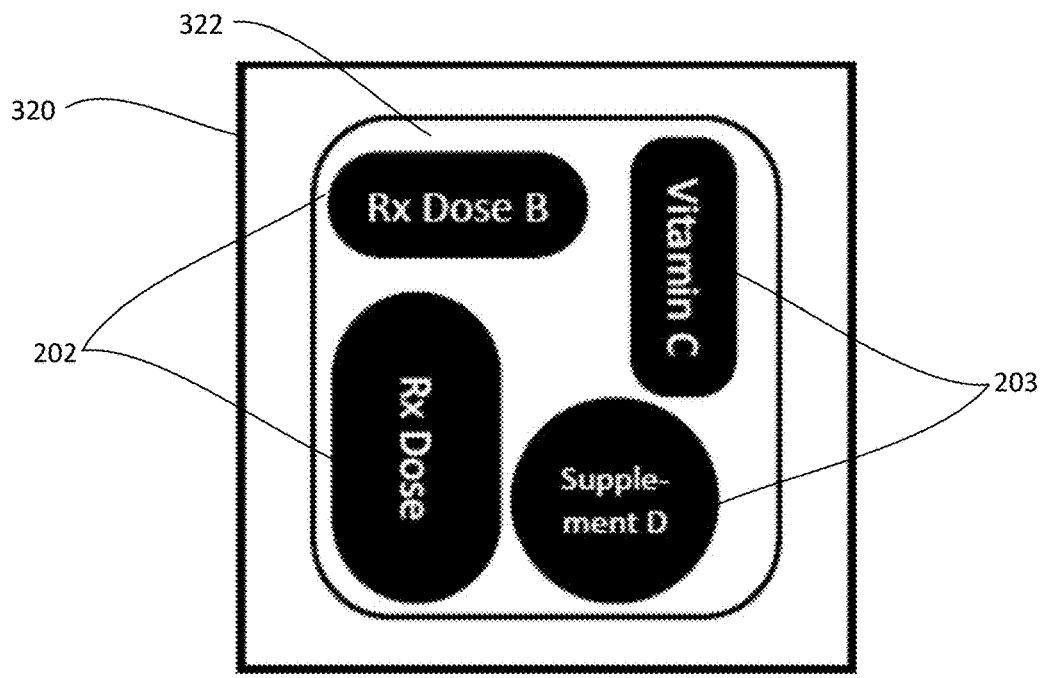
FIG. 3E.1
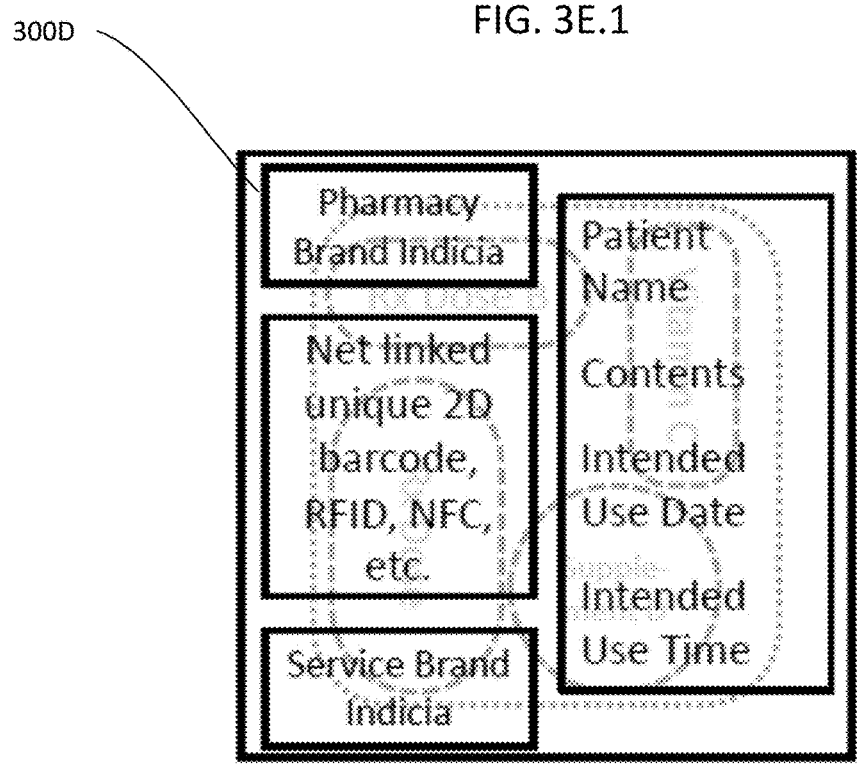
FIG. 3E.2

AUTHENTICATION METHODS AND SYSTEMS FOR DISPENSED PRESCRIPTIONS

CROSS-REFERENCE TO RELATED APPLICATIONS

This application claims the benefit of U.S. Provisional Patent Application No. 62/918,863 filed on Feb. 14, 2019; which is herein incorporated by reference in entirety.

FIELD OF INVENTION

The present invention relates to a system and method for the traceability of single dose medications, and specifically to a system and method to facilitate the traceability of dispensed pills, patches, vials, and so forth.

BACKGROUND

The present dispensing, tracking and use of prescription drugs systems in place are limited in scope with regards to understanding the compliance and adherence to the use of prescription drugs, as well as the ability to accurately track medications and their use after the prescription drugs have been disseminated by a pharmacist, medical doctor or other health care provider authorized to disseminate prescription drugs. As a result of the limited scope and tracking coupled with other incentives for individuals and businesses in the supply chain accountability has been limited, which in turn has in part contributed to widespread problems, such as the opioid epidemic that is currently affecting millions of lives.

The present application seeks to provide solutions to some of the above problems including addressing patient compliance and adherence to prescription drugs, improved tracking of prescription drugs from manufacturing to final use, authentication of prescription drugs in view of counterfeit products, identification of the sourcing of both authentic and counterfeit prescription drugs.

BRIEF SUMMARY

In at least one embodiment described herein exists a method for authenticating dispensed medications comprising the steps of providing an outside authenticator on a blister pack over at least one dose of medication and providing an inside authenticator located on the inside cavity of at least one dose of medication of the blister pack. The inside authenticator can be such that it is not completely viewable until the blister pack or individual cavity/blister of the blister pack is opened.

Each of authenticators mentioned can be comprised of a universal unique identifier, encoded into a 2-D barcode, RFID, NFC or other radio frequency or electromagnetic spectrum emitting or reflective device and at least two of the following: drug brand indicator, regional authorization indicator, and authenticator brand indicator.

The outside and inside authenticators of each blister pack can be recorded and associated with each respective dose of medication of the blister pack or other dose container in a database. The database can be utilized for authenticating purposes when the authenticator indicia are scanned.

An authenticating communication system can be provided to receive scanned information from the outside or inside authenticators from an end user utilizing a third-party scanning tool.

The authentication communication system can request from the end user permission to associate a user profile account associated with the end user with the scanning event.

Upon granting permission to associate the user profile of the end user with the scanning event a secure two-way communication connection is established between the end user and the authentication communication system.

The end user can request and receive medication prescription and adherence information associated with each dose through the authentication communication system. The medication adherence information can include any of the following: time since last dose, time until next dose, time to renew prescription, number of doses remaining, and reminder notifications associated with future doses.

The end user through a connection with the authentication communication system can invite medical professionals or support persons to view medication adherence information associated with one or more prescriptions associated with the user profile and compliance information associated with one or more prescriptions.

The authentication communication system can establish a two-way communication connection via the authentication communication system between the end user and the invited medical professional or support person.

The authentication communication system can be comprised of one or more processors associated with a set of computer executable instructions in memory configured to received scanned information and location information associated with the outside and inside authenticator associated with each dose, utilize the database comprising stored information about outside and inside authenticators associated with each dose for authentication determinations, generate and store user profile information associated with a plurality of end users in a user profile database, and create secure connections between end users and medical professionals or support persons.

The request to receive medication prescription and adherence information from the authentication communication system can further comprise entering the pharmacy phone number and the pharmacy unique prescription number, wherein the entering step can be performed by scanning the pharmacy label or manually typing/entering the information into the authentication communication system.

Another embodiment for a method for authenticating dispensed medications comprises the steps of providing an outside authenticator on a blister pack over at least one dose of medication, wherein the outside authenticator has a unique identification number associated there with and wherein each unique identification number is associated with each dose of medication and stored in a database; providing an authentication communication system having one or more processors configured to execute computer readable instructions stored in memory, wherein the authentication communication system is configured to receive scanned information associated with the outside authenticator from an end user utilizing a third-party scanning tool.

Similarly, to the first embodiment the inside authenticator can be disposed within a cavity portion of the blister pack, such that the inside authenticator is not viewable until the blister pack is opened.

Additionally, and alternatively, an on-dose authenticator can be disposed on the dose of medication that is disposed within a cavity portion of the blister pack or other type of dose container such as a pill pack.

Another embodiment for a medication authentication system comprises a dose container system having at least dose package having at least one cavity configured to store multiple pills therein, wherein a first authenticator is disposed on a human observable surface disposed over at least a portion of the cavity; a database configured to store a unique identification number associated with the first authenticator and the multiple pills; and an authentication communication system including a set of computer executable instructions disposed in memory and executable by one or more processors configured to perform at least the following steps: receiving scanned information associated with the first authenticator from an end user utilizing a third-party scanning tool.

A second authenticator can be disposed on an inner sidewall of each cavity of each dose package. The dose package system can comprise of a plurality of dose packages each having at least one cavity to store multiple pills therein, and wherein the pills can be any combination of vitamins, supplements, and doses of medication.

In some variants a housing can be configured to store the plurality of dose packages, and a second authenticator indicia is disposed on an outer surface of the housing. Such that housing authenticator and the authenticators on each of the dose packages can be scanned together for authenticity purposes as well as establishing a secure two-way communication the authentication communication system.

Another variant of the above includes a second authenticator disposed on an opposite side of the dose package system relative to the first authenticator indicia.

DETAILED DESCRIPTION

One of the objectives of the present invention is to provide an authentication methodology and assistance to help end users, providers, manufacturers, auditors, and potentially regulators to determine the authenticity of an individual dose of medication. This is of particular importance when the dose of medication has potentially addictive properties, such as various opioid medications. As result of the addictive nature of certain medications, there is an opportunity to abuse and misappropriate those medications to individuals who are not authorized to be in possession of such medications. Therefore, what is needed, is a system and method that will allow for the traceability of individual medications from manufacture, through distribution, dispensing to patients and beyond, so that the diversion of medication may be reduced, and illegal (counterfeit or imported) medications identified.

Another objective of the present invention is to establish a secure communication with end users and an authentication communication system that can further be utilized to communicate with medical providers, support persons, and provide information and compliance information as well as track compliance for appropriate adherence to the medical script provided.

Other objectives will also be noted to those of ordinary skill in the art as the various embodiments of systems and methods are described below.

In some embodiments, the methods and systems described herein relate to the secure tracking, authentication, adherence, and disposal of prescribed medications. Before describing such methods and systems in detail, however, a description is provided of a computer and a network in which such methods and systems may be implemented.

Figure 1A:
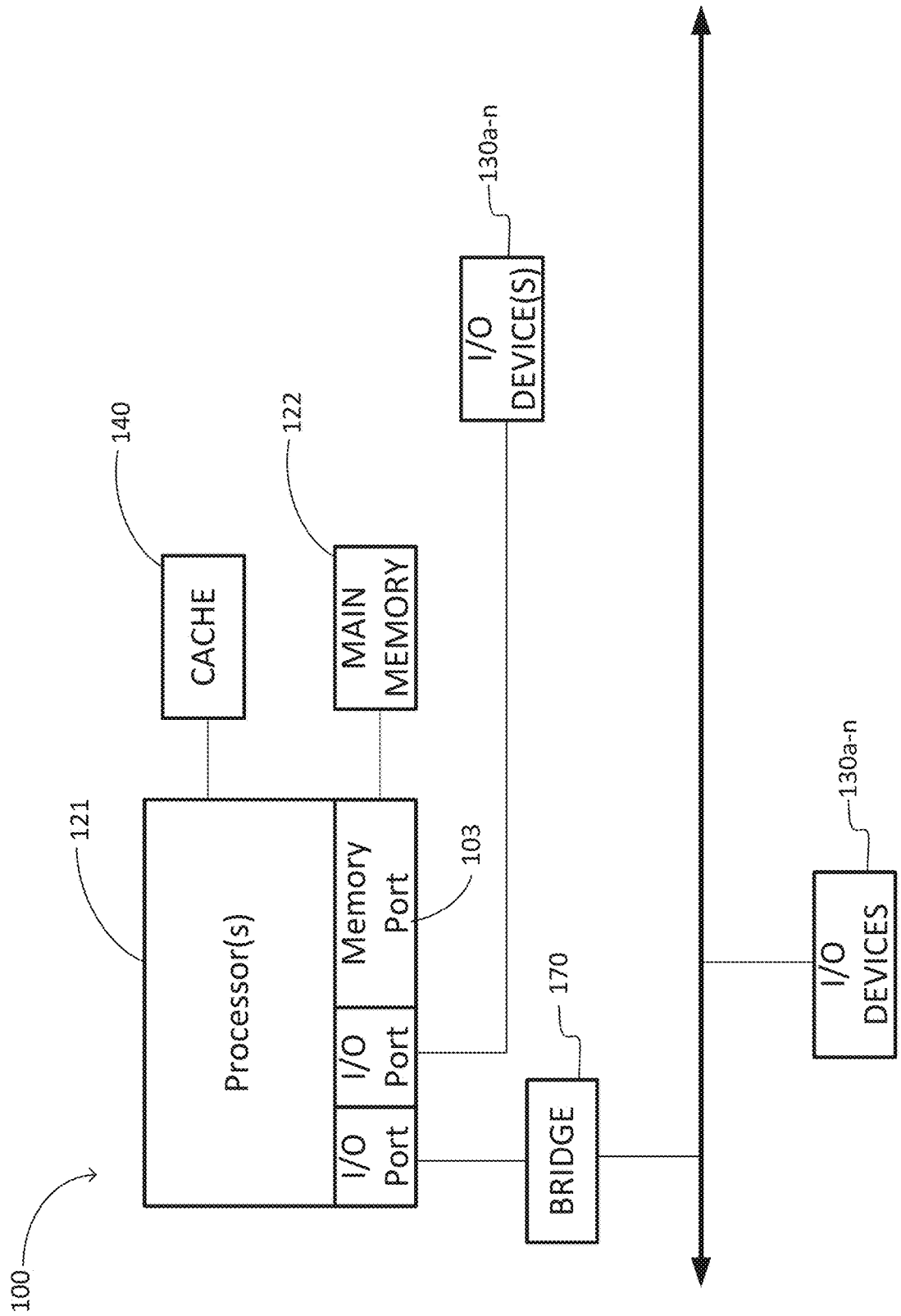
FIGS. 1A-1C are block diagrams depicting embodiments of computers, databases and networked systems useful in connection with the methods and systems described herein.
Figure 1B:
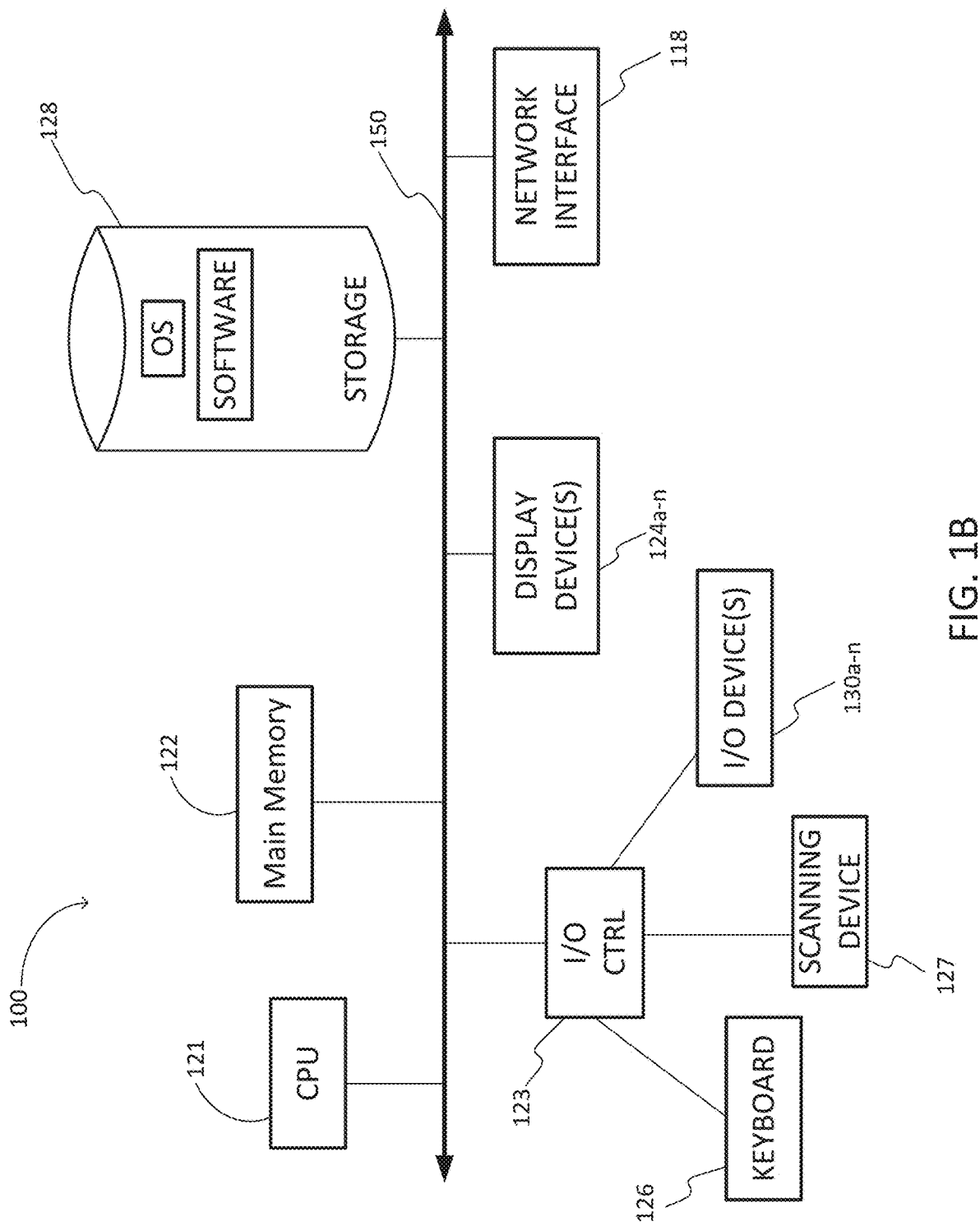

Referring to FIGS. 1A and 1B depict block diagrams of a computing device 100 useful for practicing an embodiment of the user interface 102a-c or a computing device 106a-c. As shown in FIGS. 1A and 1B, each computing device 100 includes a central processing unit 121, and a main memory unit 122. As shown in FIG. 1B, a computing device 100 may include a storage device 128, a network interface 118, an I/O controller 123, display devices 124a-n, a keyboard 126, a scanning device 127, such as a camera or 2D barcode scanner, and one or more other I/O devices 130a-n such as a mouse, trackpad, pen, RFID reader/writer and so forth. The storage device 128 may include, without limitation, an operating system and software. As shown in FIG. 1A, each computing device 100 may also include additional optional elements, such as a memory port 103, a bridge 170, one or more input/output devices 130a-n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided with one or more microprocessor units such as: those manufactured by Intel Corporation, Motorola Corporation, International Business, Advanced Micro Devices, Qualcomm. The computing device 100 may be based on any of these processors, or any other processor capable of operating as described herein.

Main memory unit 122 may be one or more memory chips capable of storing data and allowing any storage location to be directly accessed by the microprocessor 121. The main memory 122 may be based on any available memory chips capable of operating as described herein. In the embodiment shown in FIG. 1B, the processor 121 communicates with main memory 122 via a system bus 150. FIG. 1A depicts an embodiment of a computing device 100 in which the processor communicates directly with main memory 122 via a memory port 103. FIG. 1A also depicts an embodiment in which the main processor 121 communicates directly with cache memory 140 via a secondary bus, sometimes referred to as a backside bus. In other embodiments, the main processor 121 communicates with cache memory 140 using the system bus 150.

In the embodiment shown in FIG. 1B, the processor 121 communicates with various I/O devices 130 via a local system bus 150. Various buses may be used to connect the central processing unit 121 to any of the I/O devices 130, including a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display 124, the processor 121 may use an Advanced Graphics Port (AGP) to communicate with the display 124. FIG. 1A depicts an embodiment of a computer 100 in which the main processor 121 also communicates directly with an I/O device 130b via, for example, HYPERTRANSPORT, RAPIDIO, or INFINIBAND communications technology.

The computing device 100 may comprise or be connected to one or more of a wide variety of I/O devices 130a-130n, each of which may be of the same or different type and/or form. Input devices include keyboards, mice, trackpads, trackballs, microphones, scanners, cameras, RFID readers/writers and drawing tablets. Output devices include video displays, speakers, inkjet printers, laser printers, and dye-sublimation printers. The I/O devices may be controlled by an I/O controller 123 as shown in FIG. 1B. Furthermore, an I/O device may also provide storage and/or an installation medium for the computing device 100. In some embodiments, for example, the computing device 100 may provide USB connections (not shown) to receive handheld USB storage devices.

Referring still to FIG. 1B, the computing device 100 may support any suitable installation device (Not Shown), such as a floppy disk drive for receiving floppy disks such as 3.5-inch disks, 5.25-inch disks or ZIP disks, a CD-ROM drive, a CD-R/RW drive, a DVD-ROM drive, tape drives of various formats, USB device, hard-drive or any other device suitable for installing software and programs. The computing device 100 may further comprise a storage device, such as one or more hard disk drives or redundant arrays of independent disks, for storing an operating system and other software.

Furthermore, the computing device 100 may include a network interface 118 to interface to the network 104 through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, IEEE 802.11, IEEE 802.11a, IEEE 802.11b, IEEE 802.11g, IEEE 802.11n, CDMA, GSM, WiMax, and direct asynchronous connections). In one embodiment, the computing device 100 communicates with other computing devices 100' via any type and/or form of gateway or tunneling protocol such as Secure Socket Layer (SSL) or Transport Layer Security (TLS). The network interface 118 may comprise a built-in network adapter, network interface card, PCMCIA network card, card bus network adapter, wireless network adapter, USB network adapter, modem, or any other device suitable for interfacing the computing device 100 to any type of network capable of communication and performing the operations described herein.

In further embodiments, an I/O device 130 may be a bridge between the system bus 150 and an external communication bus, such as a USB bus, a FireWire bus, an Ethernet bus, a Gigabit Ethernet bus, a HIPPI bus, a Super HIPPI bus, a SerialPlus bus, a SCI/LAMP bus, a FibreChannel bus, or a Serial Attached small computer system interface bus, or any other type of bus currently available or to be created using the same architecture.

A computing device 100 of the kind depicted in FIGS. 1A and 1B typically operates under the control of operating systems, which control scheduling of tasks and access to system resources. The computing device 100 can be running any operating system such as any of the versions of the MICROSOFT WINDOWS operating systems, UNIX and LINUX operating systems, any version of the MAC OS, ANDROID operating system, IOS operating system, any real-time operating system, any open source operating system, any proprietary operating system, any operating systems for mobile computing devices, or any other operating system capable of running on the computing device and performing the operations described herein.

Figure 1C:
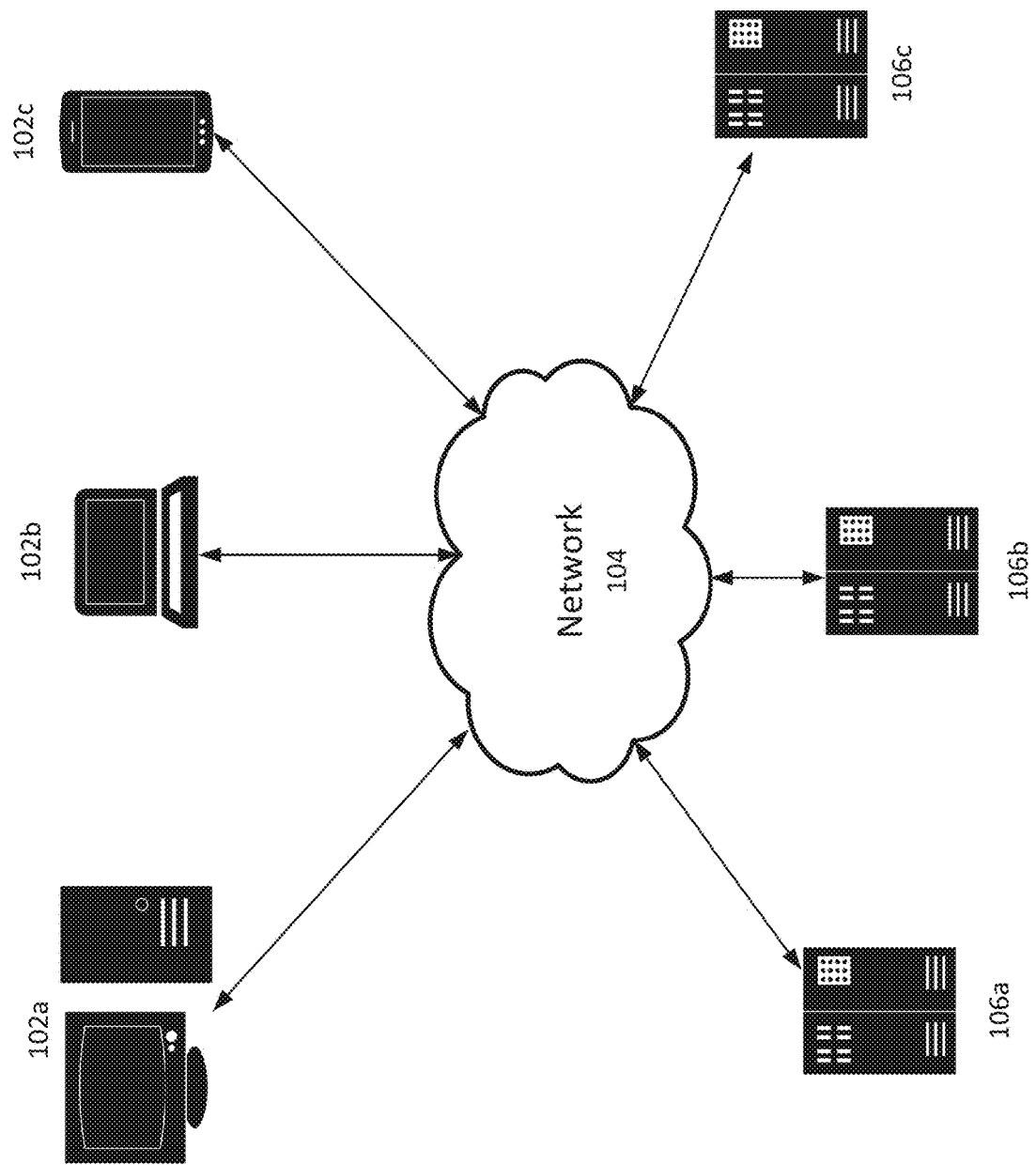

FIG. 1C illustrates an embodiment of a network environment. The network environment comprises one or more clients 102a-102c (also generally referred to as local machine(s) 102, client(s) 102, client node(s) 102, client machine(s) 102, client computer(s) 102, client device(s) 102, computing device(s) 102, endpoint(s) 102, or endpoint node(s) 102) in communication with one or more computing devices 106a-106c (also generally referred to as server(s) 106 or computing device(s) 106) via one or more networks 104.

The network 104 (also generally referred to as network(s) 104) can be a local-area network (LAN), such as a company Intranet, a metropolitan area network (MAN), or a wide area network (WAN), such as the Internet or the World Wide Web. In some embodiments, there are multiple networks 104 between the client 102 and the computing devices 106. In one of these embodiments, a network 104 may be a private network or a public network. As shown in FIG. 1C, a client 102a device on a network 104 may connect to other client devices 102b-c or to other computing devices 106a-c via one or more networks 104.

The network 104 may be any type and/or form of network and may include any of the following: a point to point network, a broadcast network, a wide area network, a local area network, a telecommunications network, a data communication network, a computer network, an ATM (Asynchronous Transfer Mode) network, a SONET (Synchronous Optical Network) network, an SDH (Synchronous Digital Hierarchy) network, a wireless network, and a wireline network. The network may comprise mobile telephone networks utilizing any protocol or protocols used to communicate among mobile devices, including AMPS, TDMA, CDMA, GSM, GPRS, or UMTS. In some embodiments, different types of data may be transmitted via different protocols. In other embodiments, the same types of data may be transmitted via different protocols.

A client 102 and a computing device 106 (referred to generally as computing devices 100) can be any workstation, desktop computer, laptop or notebook computer, server (including file servers, application servers, and media servers), portable computer, mobile telephone or other portable telecommunication device, media playing device, a gaming system, mobile computing device, smartphone or any other type and/or form of computing, telecommunications or media device that is capable of communicating on any type and form of network and that has sufficient processor power and memory capacity to perform the operations described herein. In some embodiments, the computing device 100 may have different processors, operating systems, and input devices consistent with the device.

A client 102 may execute, operate or otherwise provide an application, which can be any type and/or form of software, program, or executable instructions, including, without limitation, any type and/or form of web browser, web-based client, client-server application, HTML, an ActiveX control, or a JAVA applet, PHP and Javascript, or any other type and/or form of executable instructions capable of executing on client 102. Examples of browsers include INTERNET EXPLORER, EDGE, CHROME, FIREFOX, SAFARI and other browsers known.

A computing device 106 may be a file server, application server, web server, proxy server, appliance, network appliance, gateway, application gateway, gateway server, virtualization server, deployment server, SSL VPN server, or firewall. In other embodiments, a computing device 106 is a blade server. In further embodiments, the computing device may be a virtualized server operating one processor of a multi-processor system. In some embodiments, the functionality described herein is provided as a virtual application using a virtualized processor.

In one embodiment, a computing device 106 provides functionality of a web server. In some embodiments, a web server 106 comprises an open-source web server.

As will be described below various tasks and steps can be processed on one or more computing devices 106, as well as clients 102. The processes and steps can be bifurcated across each, for example, retrieval of information from the Authentication Database can performed on 106b, where request or query information can be received and analyzed by 106c. In some instances, clients 102a, b or c could also be assisting in real-time processing in the various steps or simply be the triggering device or interface to retrieve and/or initiate the processing of various steps as will be described below.

It should also be clear that the present embodiments can be based and operated in the cloud or cloud-based systems, of which several known cloud computing platforms that exist include Amazon Web Services® (AWS), Microsoft's Azure®, and IBM's Cloud®.

Figure 2A:
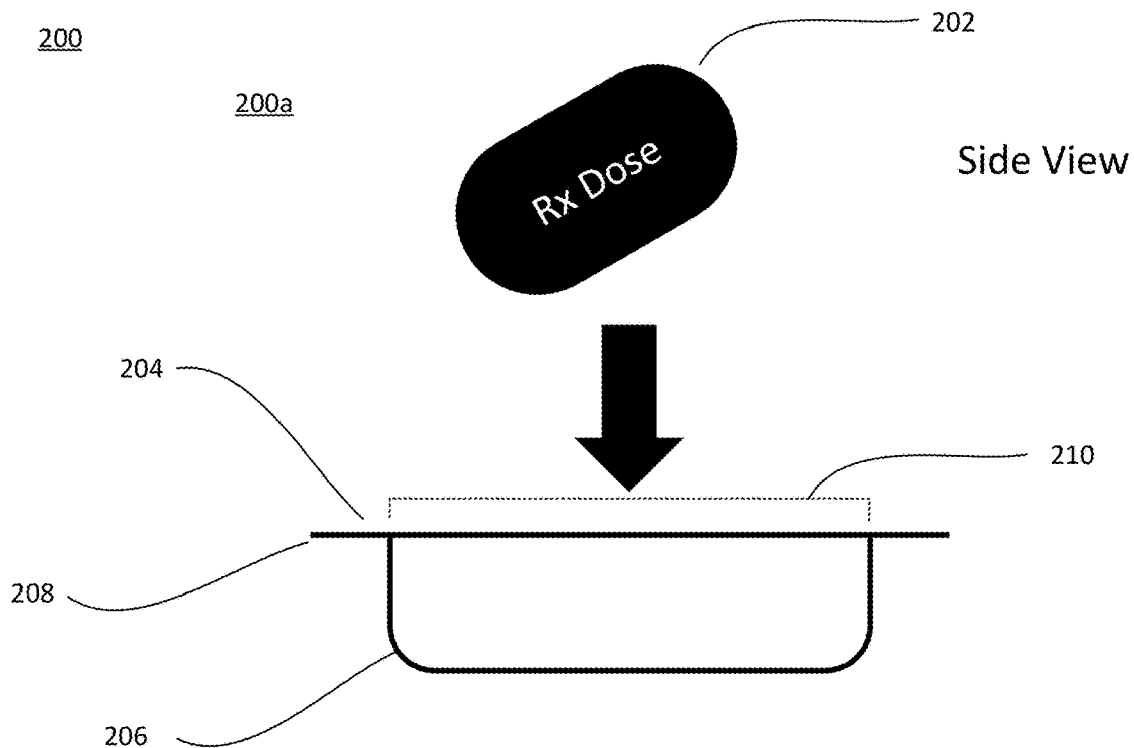
FIGS. 2A-C Illustrate various views of dose container used to store and then later dispense medications.
Figure 2B:
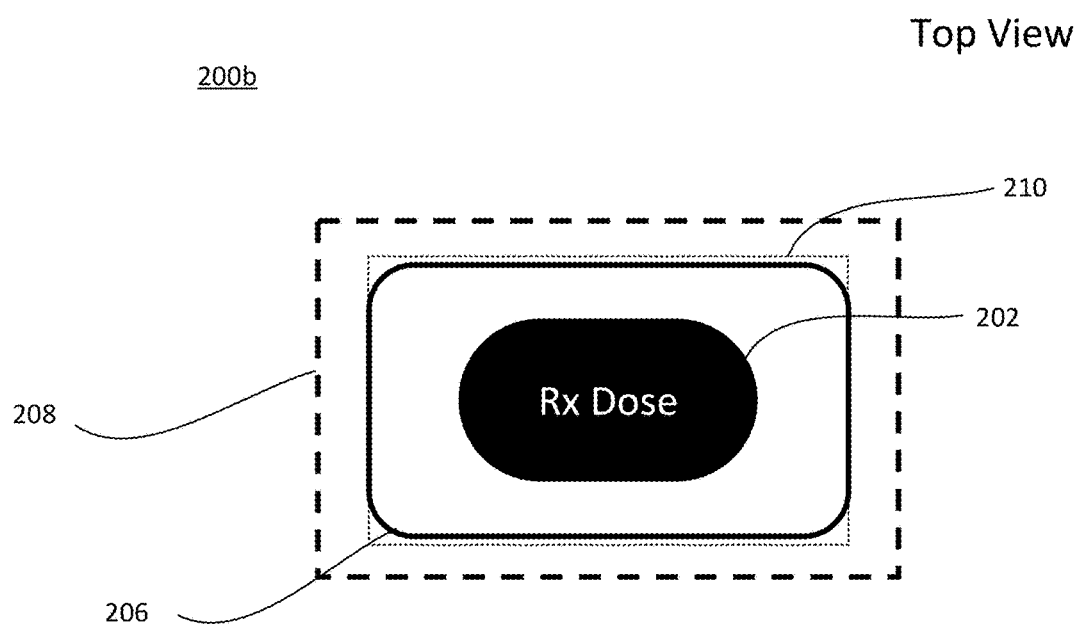

FIGS. 2A-B Illustrate various views of a dose container 200 used to store and then later dispense medication. A top view of dose container in configuration 200a is shown where a dose of medication 202 can be placed therein. FIG. 2B illustrates a configuration 200b with the dose of medication 202 disposed inside a cavity portion 206 that is connected to support layer 208. A sealing layer 204, which may be comprised of multiple layers of material, can be disposed over the support layer 208. An observable surface can be formed in part by sealing layer 204 that is provided over the cavity 206, wherein the dose of medication 202 is to be stored for shipping and later dispensing. Some common dose containers include blister packs, which can provide one or more cavity portions aligned in a matrix having X number of rows and Y number of columns. Some blister packs have different configurations such as circular shapes and so forth that are formed of the plurality of cavities or blisters. Other dose containers that are known to the those skilled in the art include rolls, jars, bottles, vials, droppers, cartridges, syringes and packets.

Figure 2C:
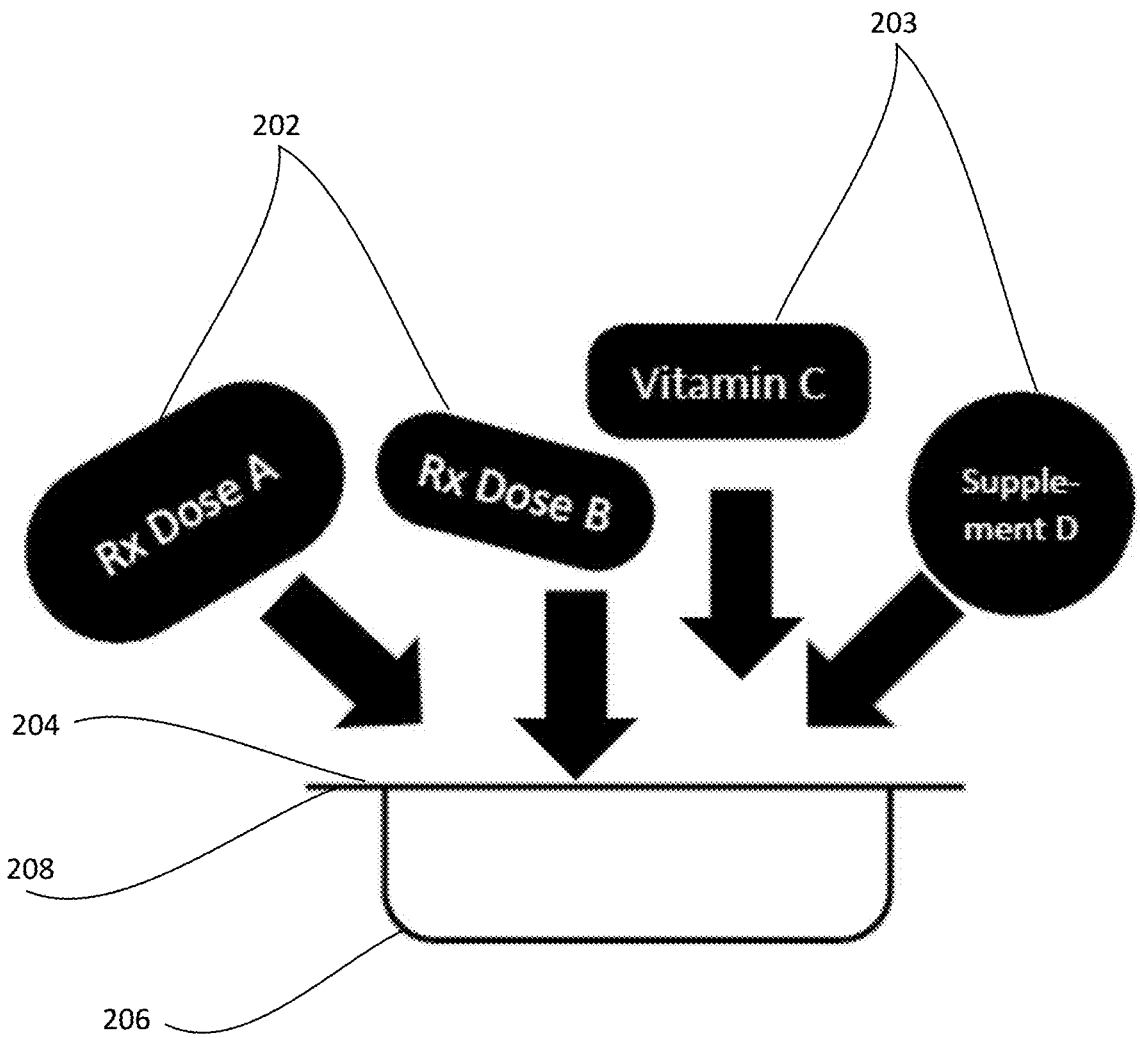

FIG. 2C illustrates another dose container like those of FIGS. 2A-C, but configured to store multiple doses of medication 202 and multiple doses of vitamins or supplements 203 in the same cavity 206. It is common for patients to take a prescribed cocktail of medications, vitamins and supplements as part of their health regiment. Increasingly there are dose containers that combine, where possible, multiple types of medications, vitamins and supplements for convenience and to assist with adherence.

An authenticator indicia, such as the example shown in FIG. 3A.1 can be disposed on or within the dose container packaging to be used as part of the systems and methods herein for authenticating doses of medication, tracking doses of medication, and establishing secure two-way communication. The authenticator indicia 300B can be comprise of one more or sections, such as section 304 that is a brand indicia, which is indicative of the manufacturer of the dose of medication, section 306 as shown can be contain a unique identification number that can be encoded into a 2D barcode or matrix, a 1-D barcode, electronically as an RFID tag, or other NFC, active or passive radio frequency tag, or electromagnetic spectrum emitting or responsive tag. Section 308 can comprise indicia associated with the brand of the service company providing the authentication systems or methods. Alternatively, a fourth indicia can be disposed thereon, such as a regional or location indicia 309. The regional indicia 309 can be indicative of an authorized distribution region, consumption region or manufacturing region where the dose of medication is allowed to be distributed to, consumed in, or manufactured in. For example, the regional indicia can include a country name or a state name, that indicates the authorized distribution of that particular dose of medication in that country or state. Thus, if a user were to see the country Japan on the authenticator indicia on a dose container and they were in the United States, it might give them pause with regards to the ability to have, distribute or consume that particular dose of medication. It might also be indicative of the governing laws or standards by which that particular dose of medication was approved or authorized. FIGS. 3A.2-3A.4 illustrate other variations and combinations for exemplary purposes, but are not intended to be limiting in scope, as additional variations can be contemplated to those skilled in the art upon presenting these examples.

Figure 3B:
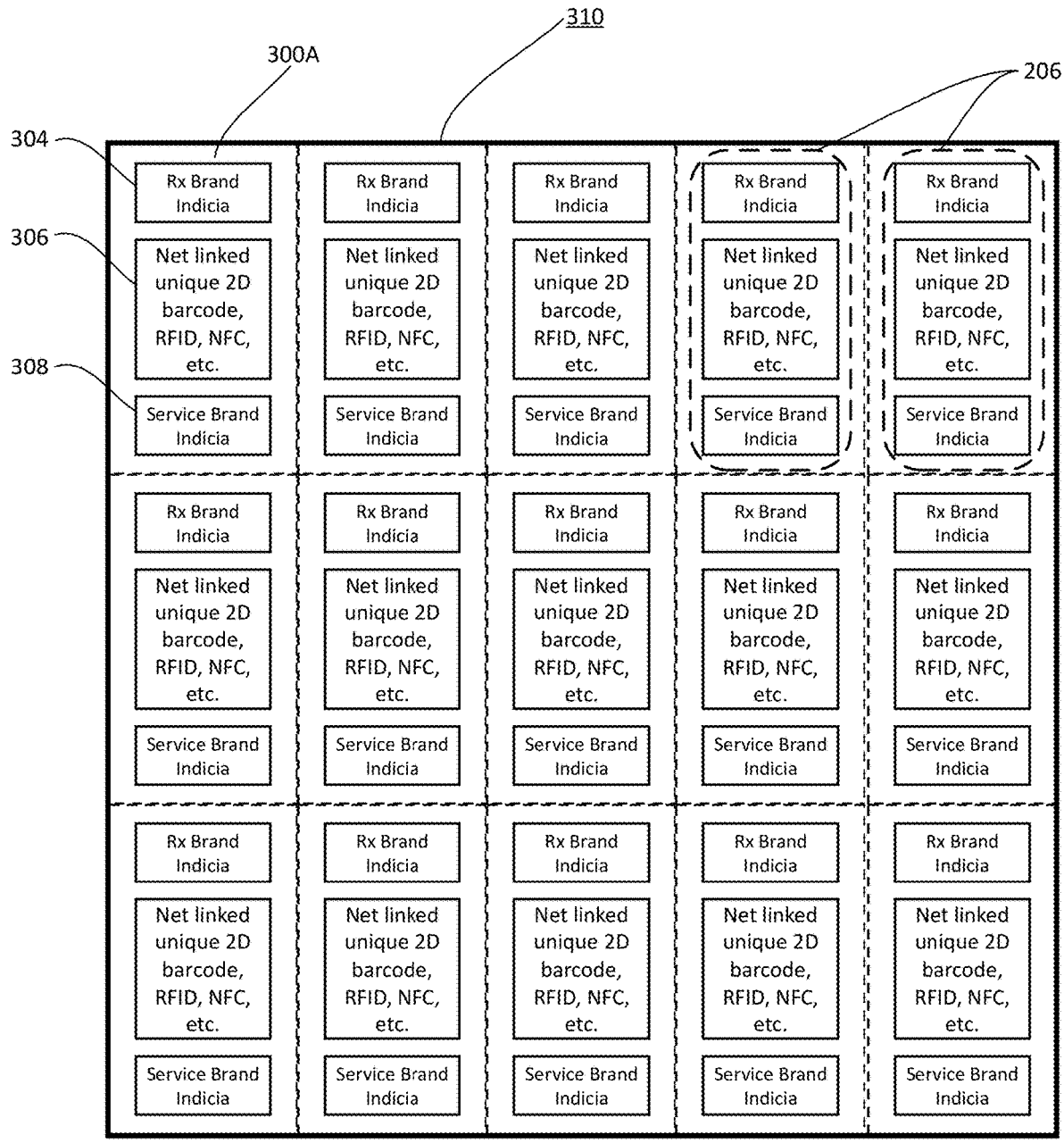
FIGS. 3A.1-C Illustrates examples of Authenticator Indicia and positions where the authenticator indicia may be placed on a dose container.
FIGS. 3D.1-3D.2 illustrate yet another example of an Authenticator Indicia being placed on to the dose of medication itself.
FIGS. 3E.1-3E.2 illustrate yet another example of an Authenticator Indicia being placed on a multi-dose/vitamin/supplement dose container.

In FIG. 3B a sheet 310 of authenticator indicia 300 can be disposed over a dose container, such as a blister pack, having a plurality of cavities 206 or blisters. The sheet 310 can formed as part of the sealing layer 204 discussed above or be a separate layer that is overlaid thereon. The authenticator indicia 300B can also be printed on, etched into, blazed into, or burned onto (using a laser or heat source) the sealing layer 204 or alternatively a portion of the sealing layer 204. In a preferred embodiment the authenticator indicia 300B are disposed over or within an observable surface that is directly or at least partially disposed over the dose of medication that is to be contained in the cavity or blister portion. These authenticator indicia shown in FIG. 3B may also be referred to as an outside authenticator 300A.

Figure 3C:
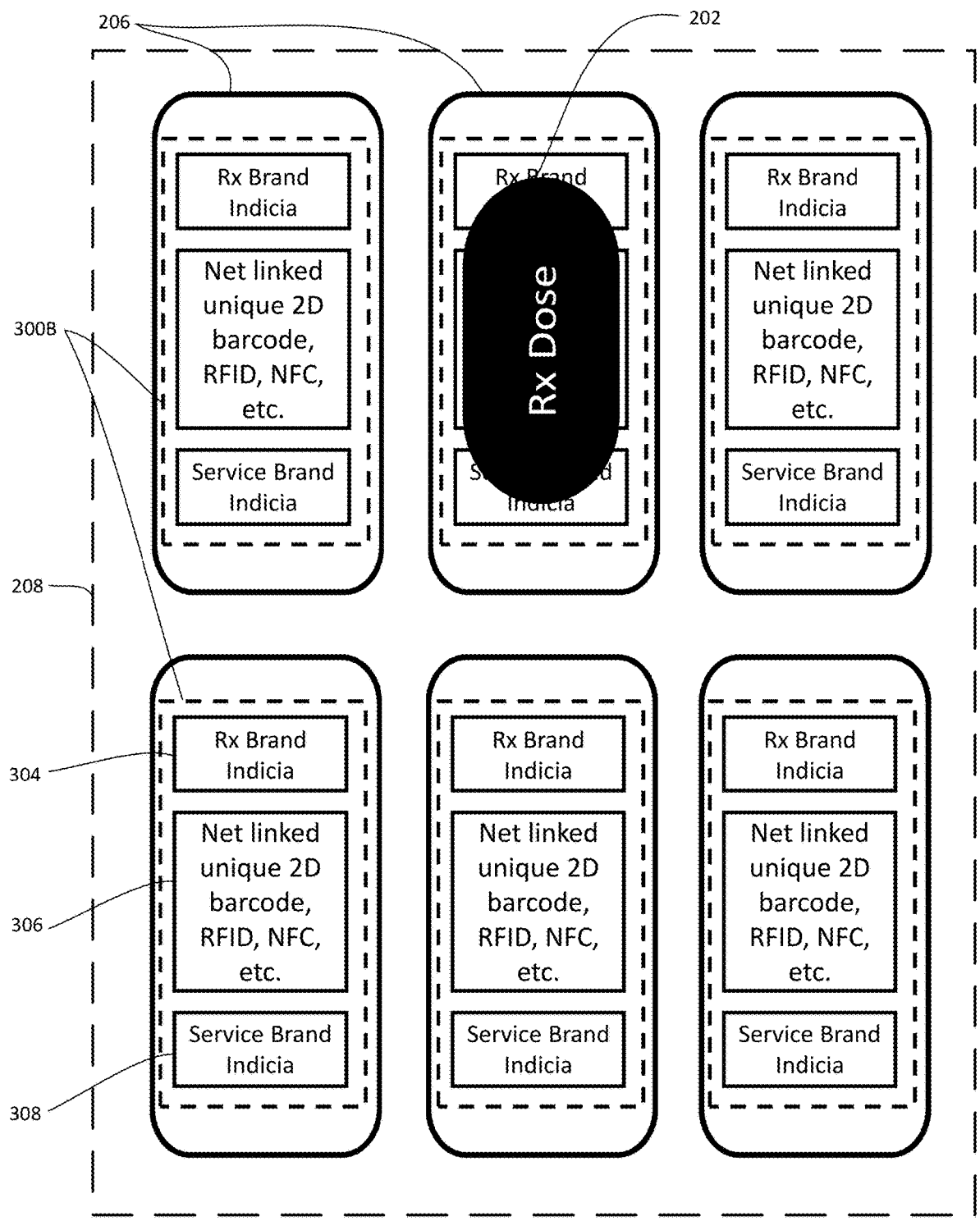

In another configuration, shown in FIG. 3C the authenticator indicia 300B can be disposed within the cavity 206, such as on the inside bottom surface of the cavity 206. As shown, when a dose of medication 202 is placed therein it can cover at least partially a portion of the authenticator from being viewed. Furthermore, when the sealing layer 204 is placed over top the cavity portion the ability to view the authenticator indicia 300B can be completely restricted. In other words, the sealing layer can be non-translucent or non-transparent layer to restrict viewing into the cavity. Alternatively, the outside authenticator 300A can block the view in addition to the dose of medication 202. The cavity or blister portion 206 can also have non-translucent, or non-transparent qualities as well.

In this configuration or location of the authenticator indicia, as shown in FIG. 3C, it can also be referred to as the inside authenticator 300B. The outside authenticator 300A and inside authenticator 300B each have their own unique identification number encoded therein. These unique identification numbers (one from 300A and one from 300B), as will be discussed in more detail below, can be associated with the single dose of medication 202 and used for authenticating the dose of medication.

FIGS. 3D.1-3D.2 illustrate yet another location or configuration of an Authenticator Indicia 300C, which is placing the Authenticator Indicia onto the dose of medication 202. The two figures shown use different shapes of doses of medication 202 to illustrate the Authenticator Indicia 300C can be adapted to various shapes and surfaces accordingly. Authenticator Indicia 300C can also be referred to as an on-dose authenticator. As disclosed so far, there can be at least a first, second and third versions of authenticators each having their own unique identification number and other indicia associated therewith. Again, additional authenticators in additional configurations and locations are possible, thus the examples are not meant to be exhaustive, but rather principles of what can be.

It should be noted that in one embodiment only a single outside authenticator is used for authenticating a dose of medication. In another embodiment only the inside authenticator is used for authenticating a dose of medication and in yet another embodiment both the outside and inside authenticators are used to authenticate the dose of medication. In yet another embodiment, the outside authenticator and the on-dose authenticator can be used. Alternatively, a first and second authenticator can be used or even a first, second and third authenticator can be used.

FIGS. 3E.1-3E.2 illustrate utilizing an authenticator indicia 300D with a dose container 320 having a cavity or pocket 322 configured to hold a plurality of medications 202 and/or vitamins/supplements 203. FIG. 3E.2 shows Authenticator indicia 300D on the outside of the dose container 320, but similar to some of the embodiments previously described an inside authenticator could be disposed on the inside of the dose container 320 for example in the cavity or pocket 322 that is only viewable upon opening the dose container 320 (though not shown). Also, as described previously one or more medications 202 or vitamins/supplements 203 could have an on-pill authenticator indicia. As noted above the dose container 320 could be a blister pack, or a pill pack, or other type of dose container that has a cavity configured to hold multiple pills. In the version of a pill pack, each pill pack can be connected along and edge and formed into a roll or tape, which is then stored in another housing or container that dispenses each pack (containing a plurality of pills) one at time, that can be separated from the rest of the roll or tape. An authenticator Indicia can be placed on the container or housing where the tape or roll of pill packs is stored.

Figure 4:
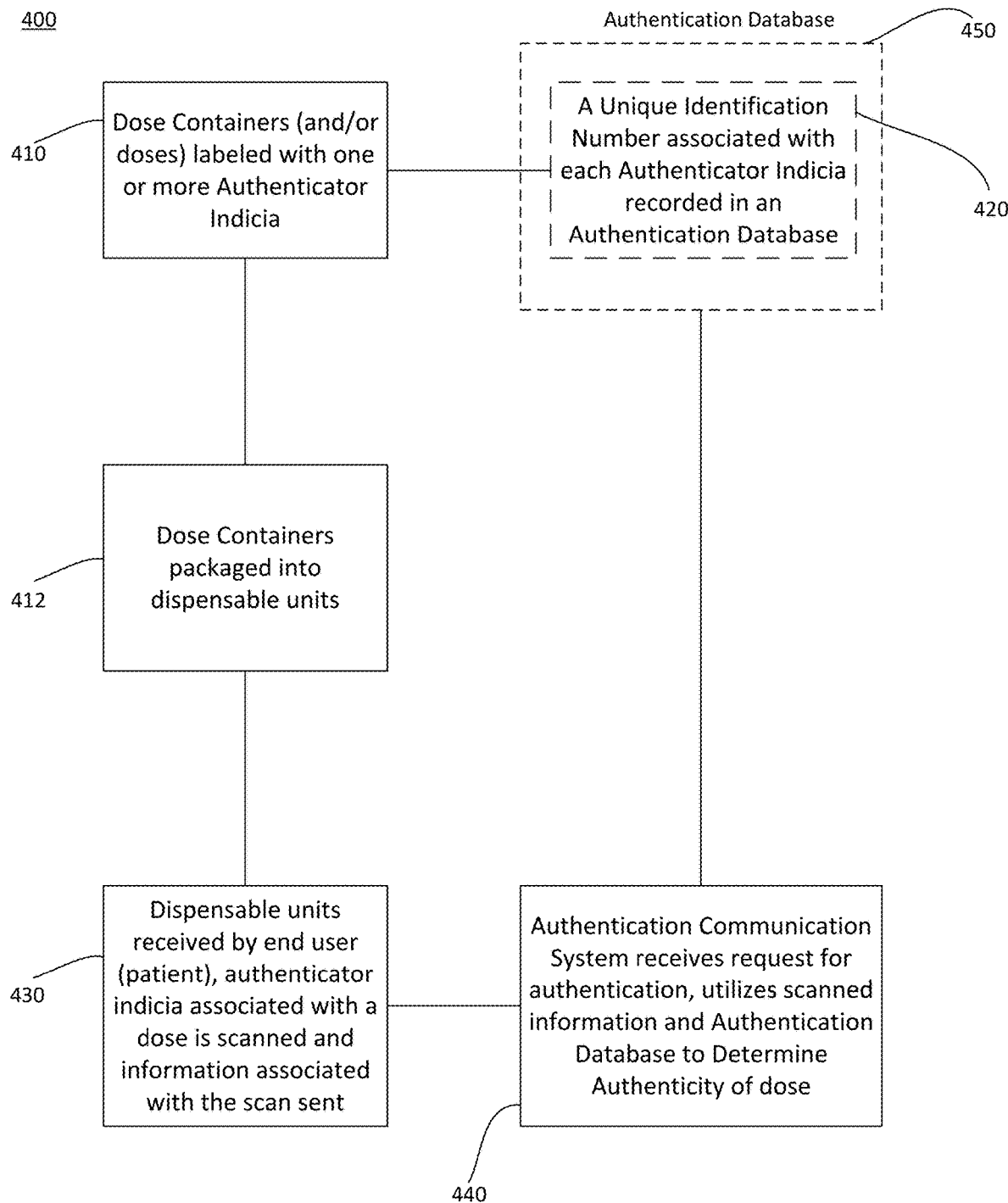
FIG. 4 illustrates a flowchart of a method of authenticating a dose of medicine.

FIG. 4 illustrates a flowchart of a method 400 of authenticating a dose of medicine. In step 410 dose containers are labeled or otherwise provided with authenticator indicia, such as 300, described above. A unique identification number that is associated with each authenticator indicia can be recorded in step 420 in an Authentication Database 450. The dose containers can then be packaged into dispensable units in step 412. Once the dispensable units are distributed, the end user, such as patient who was prescribed the medication by a medical professional, can scan the authenticator indicia and send scanned information to the Authentication Communication System in step 430. The scanned authenticator indicia and request for authentication can be received by the Authentication Communication System in step 440. The Authentication Communication system can then use the scanned authenticator indicia and information associated with the request, as well as the Authentication Database to determine the authenticity of the dose of medication. For purposes of this application it should be understood that a medical professional can include: medical doctors, nurses, pharmacists, nutritionists, dieticians, physician's assistants, dentists, optometrists, physical/occupational/addiction therapists, psychiatrists, and others that would be within this scope in view of these examples.

Figure 5A:
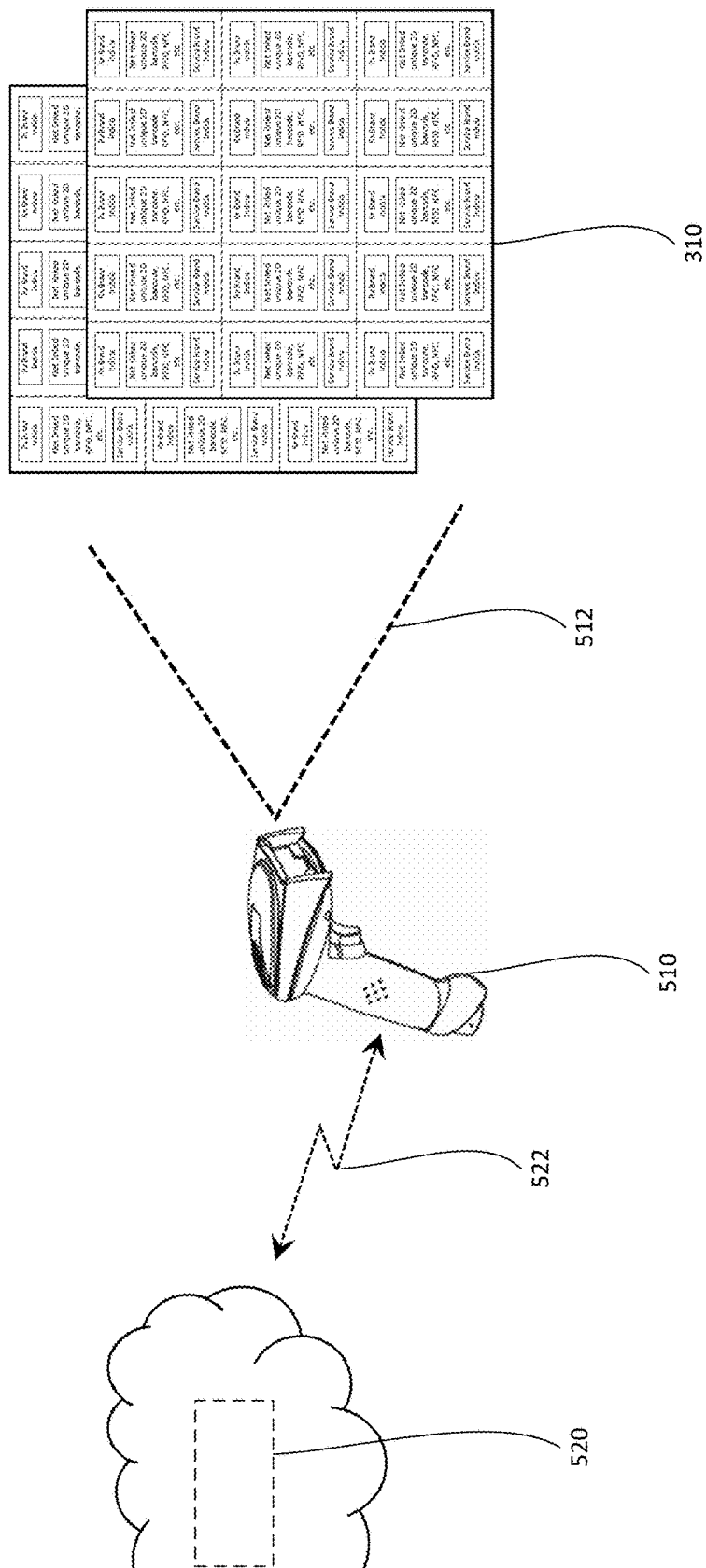
FIGS. 5A-D are various diagrams illustrating steps and systems associated with method and system for authenticating a dose of medicine.
Figure 5B:
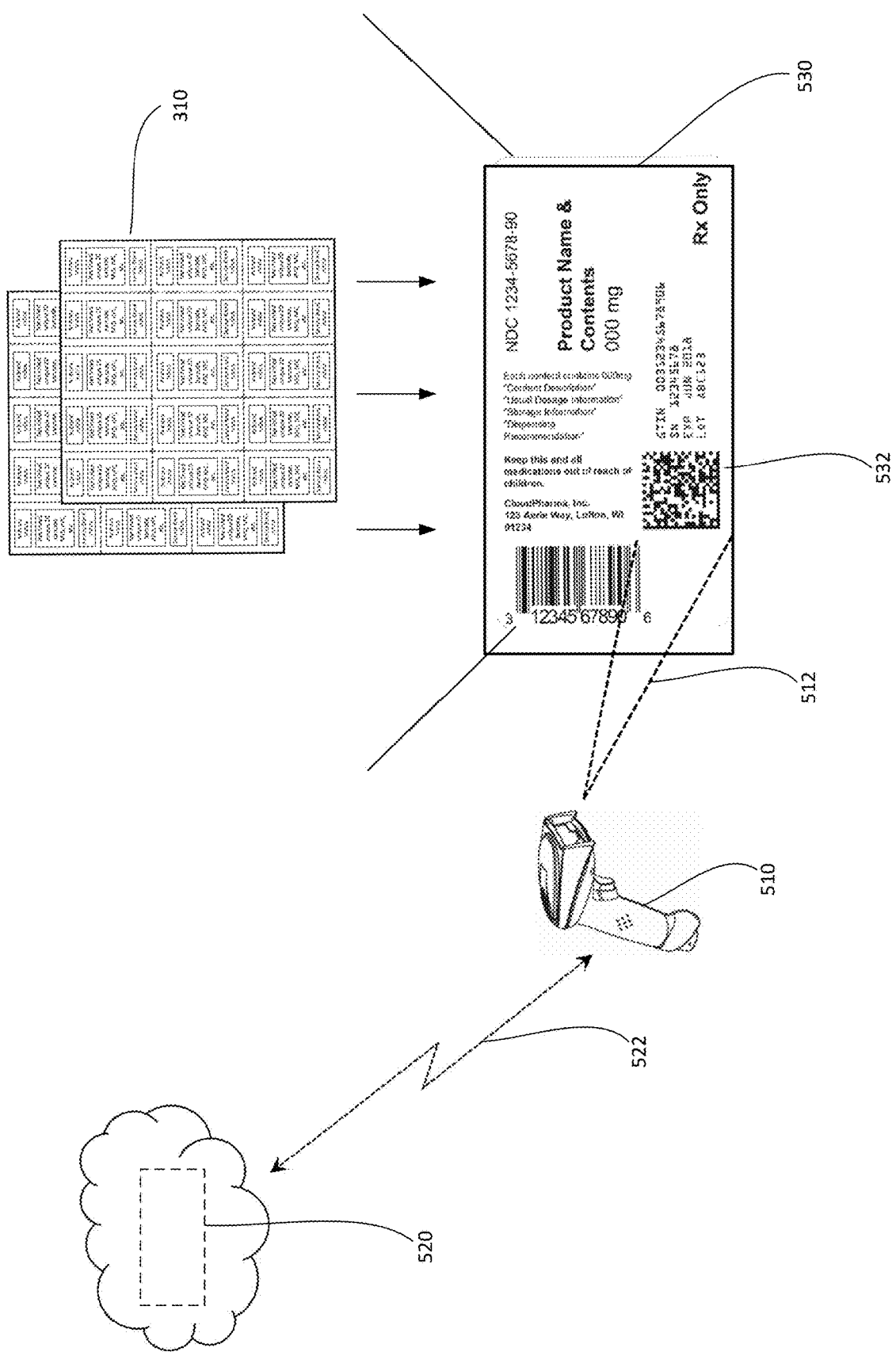
Figure 5C:
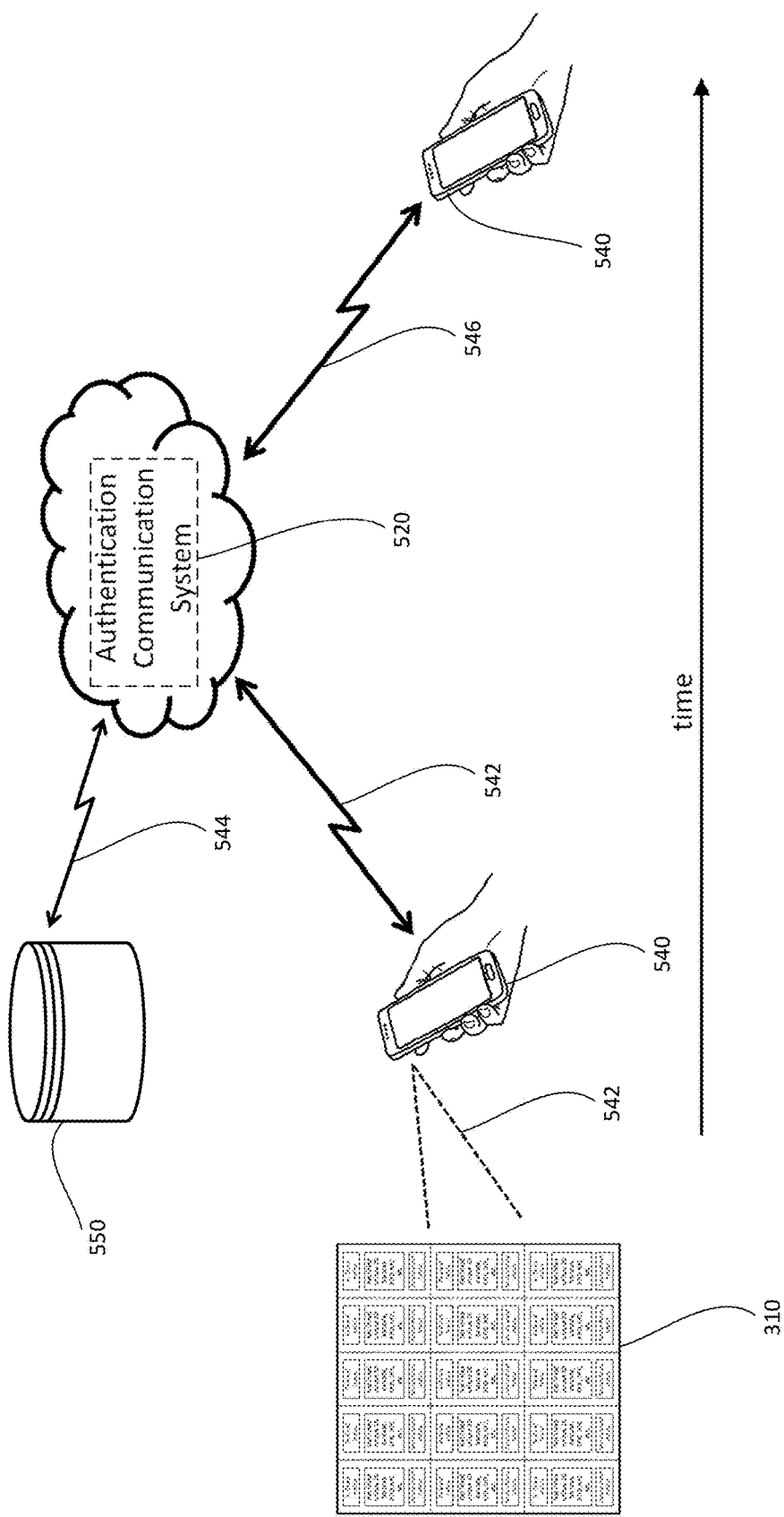

FIGS. 5A-C illustrate various structural and system components for implementing the method shown and described in FIG. 4 and above. FIG. 5A illustrates utilizing a scanning tool 510 to scan 512 one or more authenticator indicia, such as those disposed on sheet 310 disposed on a dose container, such as a blister pack. The scanned information can then be transmitted via a network 522 to an external source, such as the Authenticator Communication System 520, which can be hosted in the cloud. It should be noted that scanning tool 510 can be comprised of a variety of types including, 2D barcode scanning device, imaging camera on a smartphone, tablet or other computing device, laser scanner, printer scanner or other device utilized to detect a visual authenticator indicator. In the embodiments where the authenticator indicia have a radio or electromagnetic component, an appropriate RFID, NFC, or other radio transceiving device can be used to account for the non-visual indicia components. As noted above, the information scanned from the authenticator indicia, such as the unique identification number can be transmitted by the scanning tool or a computing device associated with the scanning to the Authenticator Communication System 520 for authentication analysis and determination. Additionally, the scanning tool can transmit location-based information derived from GPS information, IP addresses, registries, cellular network or other location-based technologies along with the unique identification number. Time, date and user information can be transmitted. Information about product, lot and purchase order can also be transmitted.

Additionally, or alternatively, an authenticator indicia 532 can be disposed on the dispensable unit packaging 530, which can be scanned and transmitted to the Authenticator Communication System 520. This could be a fourth authenticator in addition to the other authenticators described above. This dispensable unit authenticator can also have its own unique identification associated therewith.

FIG. 5C illustrates an end user utilizing a smartphone 540 having a camera or other scanning tool to scan an authenticator indicia associated with a dose of medication. The scanned information including the unique identification number and location information are transmitted 542 to the Authentication Communication System 520, which can then utilize the unique identification number along with stored information in the Authentication Database to determine the authenticity of the dose of medication. As previously noted, location information, time or date information and user information can also be utilized as part of authenticating determination process. Once an authentication determination has been realized system 520 can then transmit 546 authenticity information to a user portal accessible by smartphone 540. Additionally, and in some implementations of the system, system 520 can request access to a user profile, or the user profile associated with the end user that is prescribed the dose of medication, prior to transmitting authentication determination information.

Figure 5D:
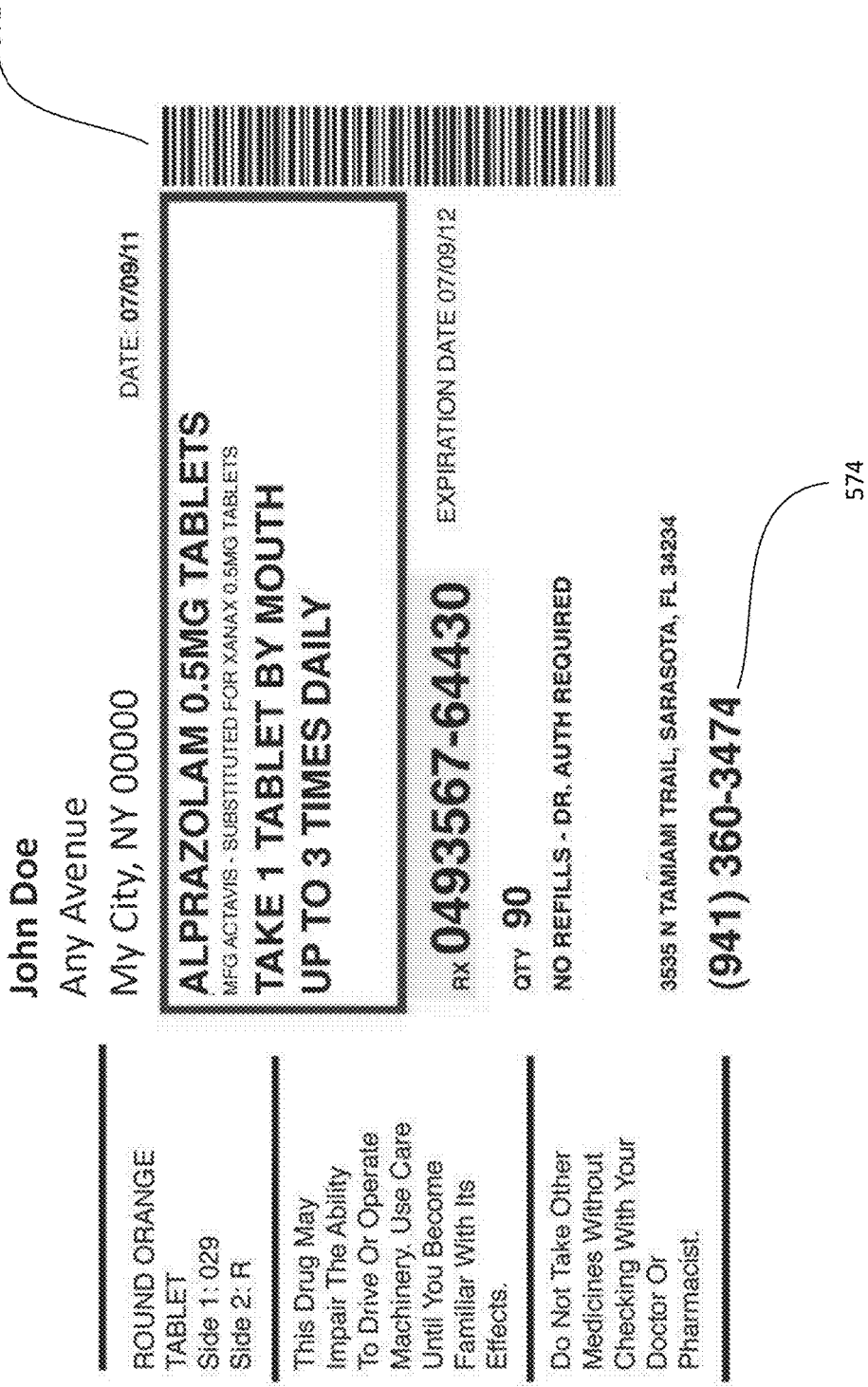

FIG. 5D illustrates a pharmacy label 570 that has a barcode 572 and a pharmacy phone number 574 listed thereon, along with additional information. The end user can utilize a scanning tool such as 510 or 540 mentioned above to scan the barcode 572 and pharmacy phone number 574 as part of the authenticating determination process. The scanned barcode 572 and pharmacy phone number 574 can assist with automatically retrieving proper dosage and usage information associated with the medical script. Often the barcodes 572 are part of internal pharmacy numbering and database system. The authentication communication system can access that information to understand the type and number of doses dispensed, the pharmacy phone number can be used to identify the type of pharmacy such as CVS, RITEAID and other sources to understand the type of pharmacy numbering system utilized for interpreting the barcode, so as to appropriately translate those numbers or to retrieve the specific prescription associated with that number. These are in addition to the authentication measures utilized for authenticity.

Figure 6A:
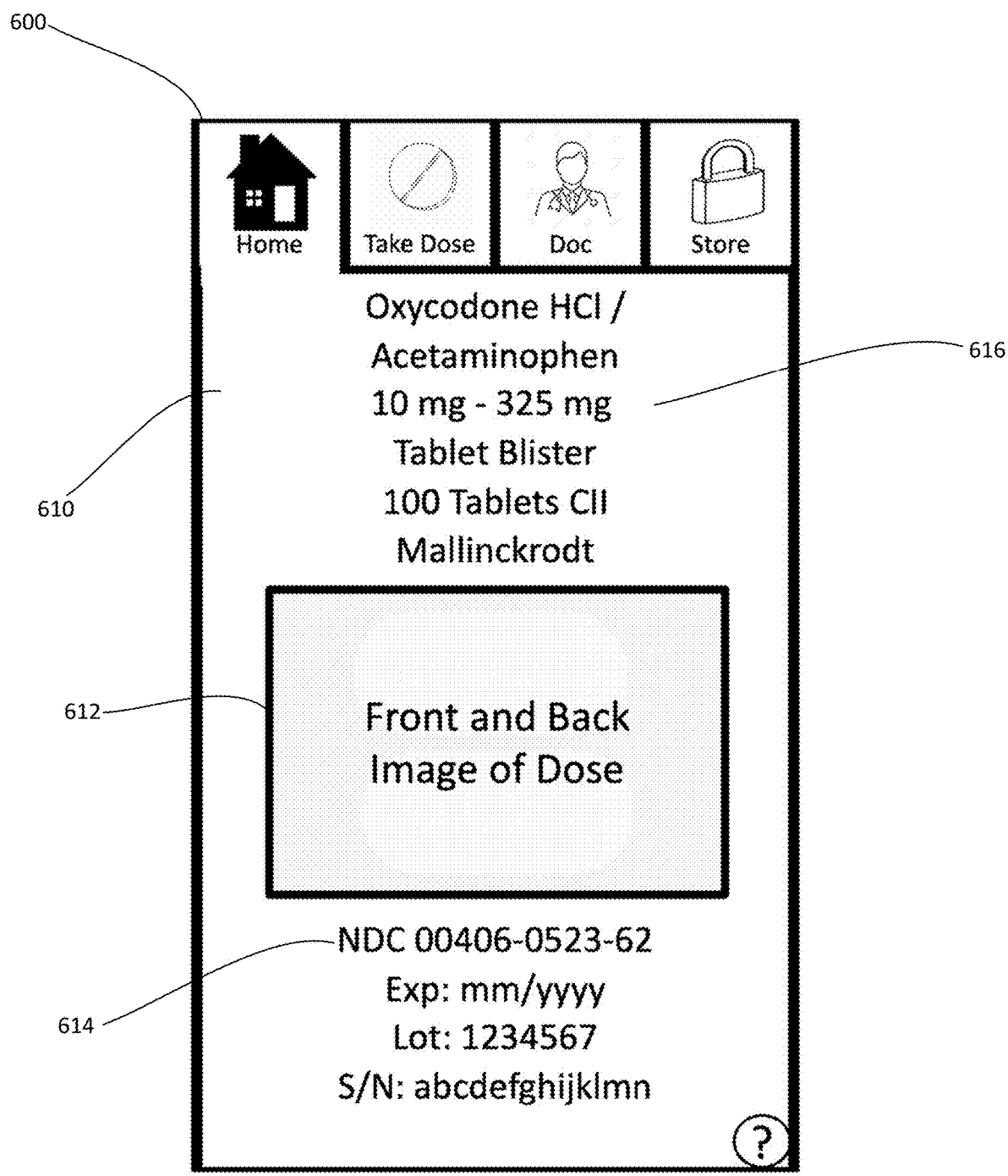
FIGS. 6A-D illustrates various screenshots of a portal used to authenticate a dose of medicine and establish a secure communication with an Authentication Communication System.

FIGS. 6A-D illustrate a user portal 600 for accessing and utilizing the Authentication Communication System. As shown in FIG. 6A, user portal 600 has can have a variety of interfaces, such as interface 610, which includes feature 612 for scanning authentication indicia associated with a dose of medication, or in more particular the feature is configured to utilize or access a scanning tool or device such as the camera of smartphone. Once a dose of medication is scanned and information sent to the Authentication Communication System, information about the dose of medication can be viewed in sections 614 and 616.

Figure 6B:
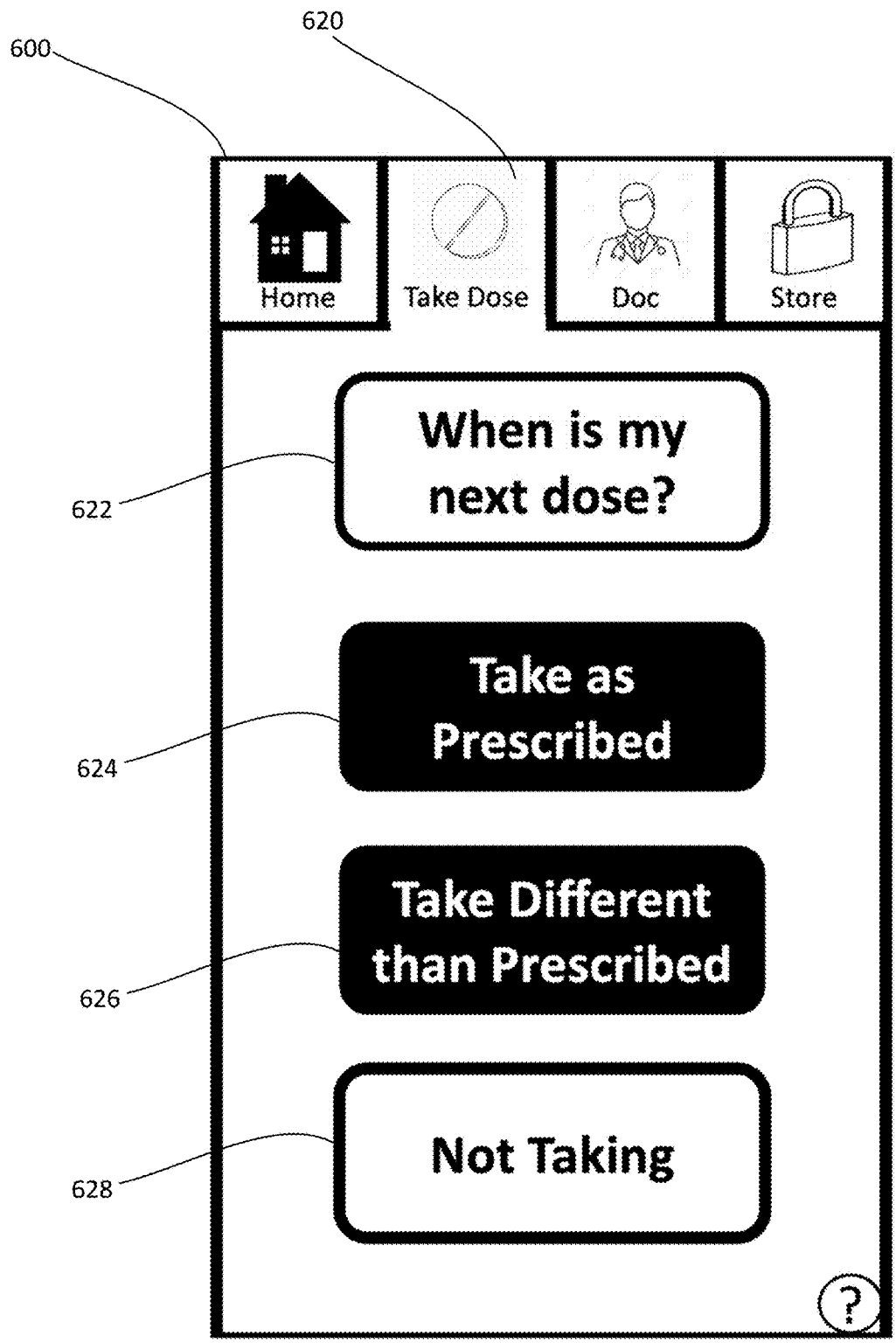

Another interface 620 shown in FIG. 6B can be utilized to communicate with the Authentication Communication System securely upon establishing upon scanning a dose of medication that has been authenticated. Interface 620 can include transmitted information from the Authentication Communication System regarding the appropriate time to take the next dose, history of previous doses taken, reminders and alerts related to taking the next dose or seeing a medical provider regarding a refill, or tracking adherence or non-adherence to the prescribed medical script. Some of these features are shown in sections 622, 624, 626 and 628 by way of example and are not limiting. This information can be stored in a database, such as a user profile database, that is accessible by the Authentication Communication System and end user.

Figure 6C:
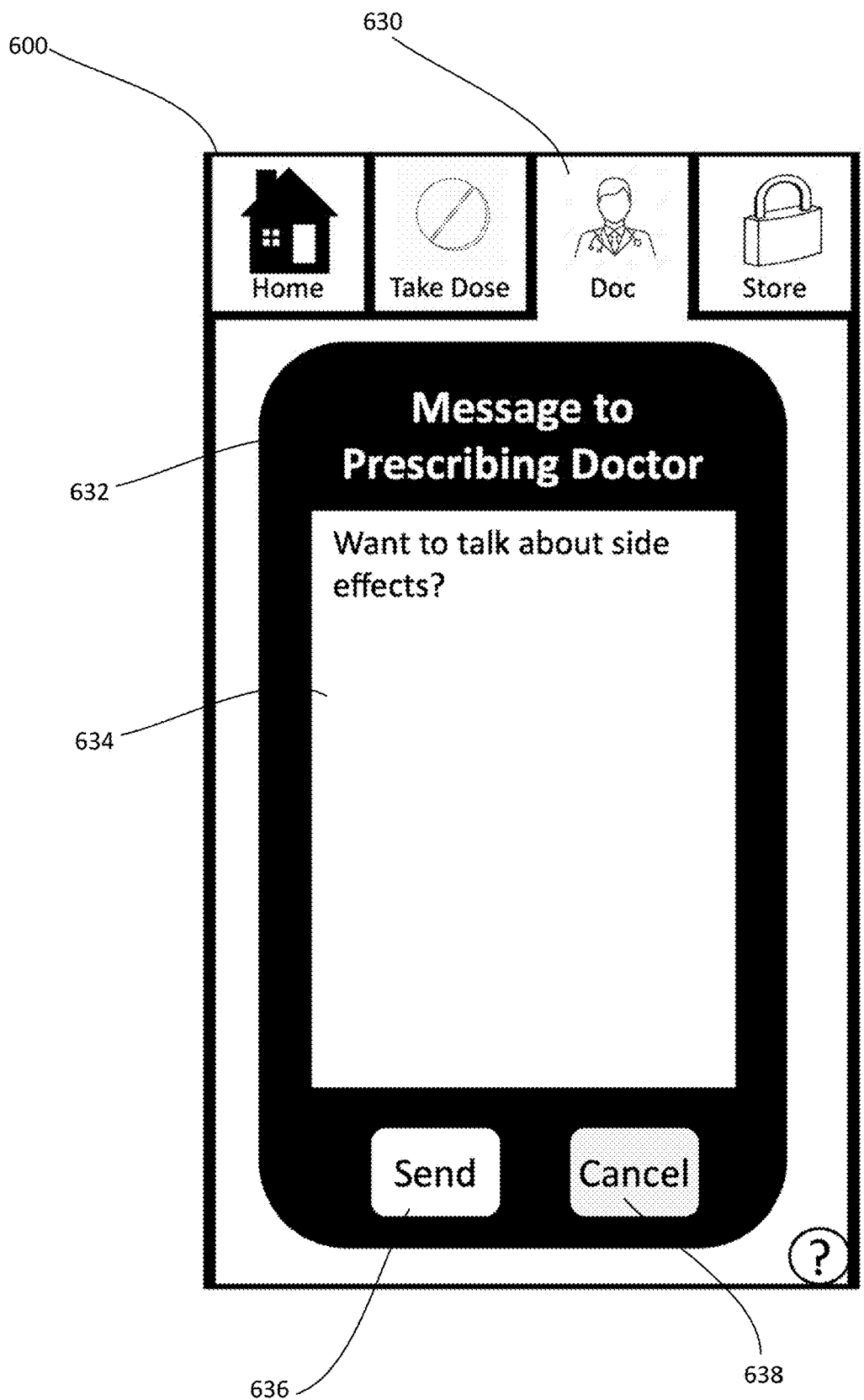
Figure 6D:
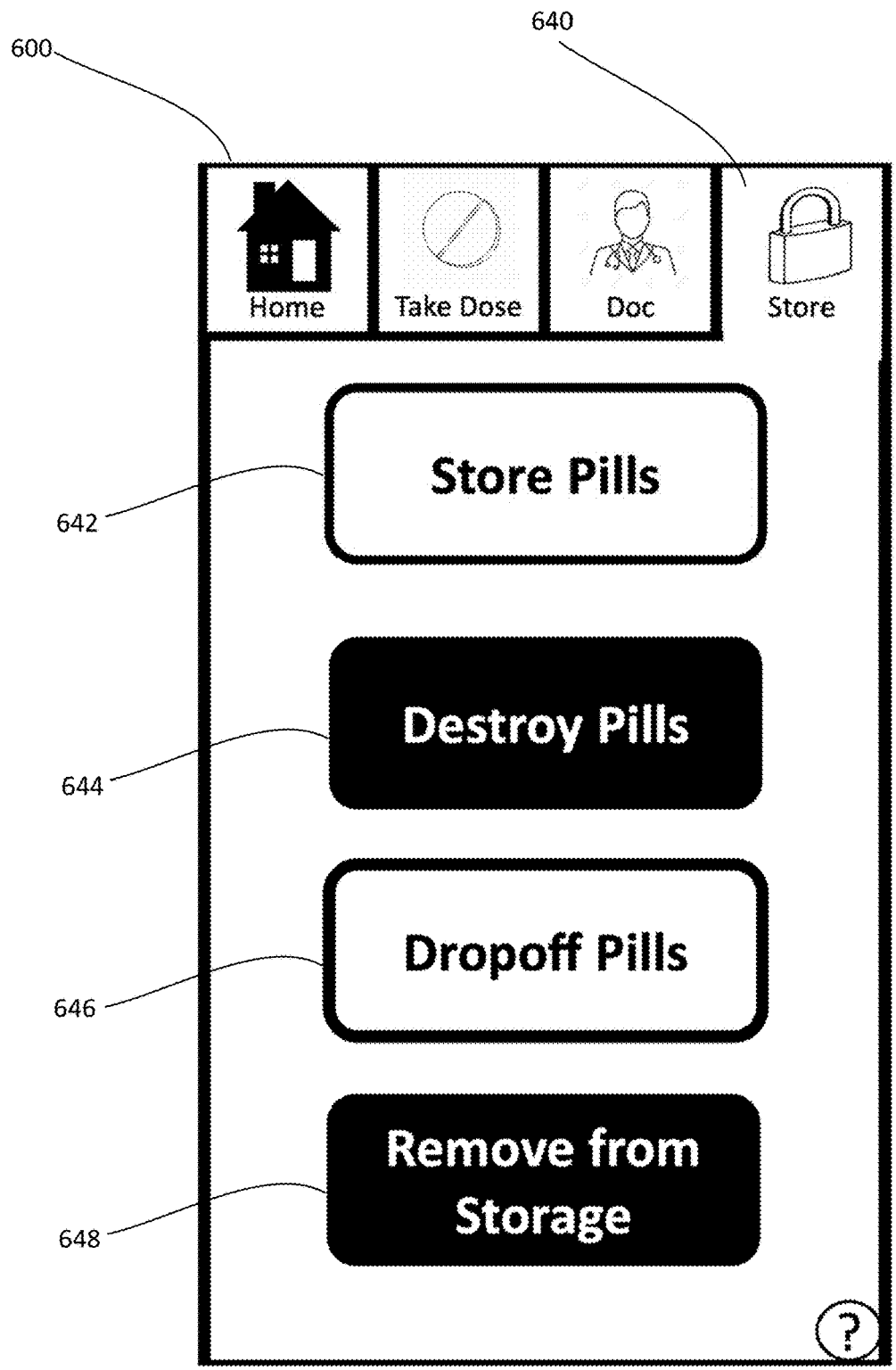

Interface 630 shown in FIG. 6C can be utilized to invite and communicate with third parties like medical providers or authorized support persons. Sections 632 provide a messaging portal 632 with a messaging section 634 and means to send 636 the message or cancel/delete 638 the message. These communications can be stored with the user profile information, stored locally on a device accessing the portal 600, or deleted instantly upon closing the portal.

Interface 640 can provide instructions and information associated with storing 642 medication, destroying medication 644, disposing of medication to a drop-off location 646, which locations nearby can be determined based on location information, and removing from storage 648.

As mentioned, the methods, systems and structure describe assist with the authenticating process of doses of medication, using authenticator indicia associated with doses of medication to establish a secure communication with an Authentication Communication System, and communicate via a portal of the Authentication Communication System with medical providers and authorized persons.

It should be understood that the systems described above may provide multiple ones of any or each of those components and these components may be provided on either a standalone machine or, in some embodiments, on multiple machines in a distributed system. The phrases 'in one embodiment,' 'in another embodiment,' and the like, generally mean that the particular feature, structure, step, or characteristic following the phrase is included in at least one embodiment of the present disclosure and may be included in more than one embodiment of the present disclosure. Such phrases may, but do not necessarily, refer to the same embodiment.

The techniques described above may be implemented as a method, apparatus, or article of manufacture using programming and/or engineering techniques to produce software, firmware, hardware, or any combination thereof. The techniques described herein may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices. As indicated above, software (also referred to herein as components, modules, programs, program code, and applications) may include virtual machines and virtualized software.

Any of the functions disclosed herein may be implemented using means for performing those functions. Such means include, but are not limited to, any of the components disclosed herein.

Each computer program within the scope of the claims below may be implemented in any programming language, such as assembly language, machine language, a high-level procedural programming language, or an object-oriented programming language. The programming language may, for example, be LISP, PROLOG, PERL, C, C++, C#, JAVA, PYTHON, HTMLS or any compiled or interpreted programming language.

Each such computer program may be implemented in a computer program product tangibly embodied in a machine-readable storage device for execution by a computer processor. Method steps of the invention may be performed by a computer processor executing computer program instructions tangibly embodied on a non-transitory computer-readable medium to perform functions of the invention by operating on input and generating output. Cookies, operating systems, and other information may also be stored on non-transitory computer-readable medium. Suitable processors include, by way of example, both general and special purpose microprocessors. Generally, the processor receives instructions and data from a read-only memory and/or a random-access memory. Storage devices suitable for tangibly embodying computer program instructions include, for example, all forms of computer-readable devices, firmware, programmable logic, hardware (e.g., integrated circuit chip; electronic devices; a computer-readable non-volatile storage unit; non-volatile memory, such as semiconductor memory devices, including EPROM, EEPROM, and flash memory devices; magnetic disks such as internal hard disks and removable disks; magneto-optical disks; and CD-ROMs). Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium. A computer may also receive programs and data from a second computer providing access to the programs via a network transmission line, wireless transmission media, signals propagating through space, radio waves, infrared signals, etc.

Having described certain embodiments of methods and systems for distribution and retrieval of network traffic records, it will now become apparent to one of skill in the art that other embodiments incorporating the concepts of the disclosure may be used. Therefore, the disclosure should not be limited to certain embodiments, but rather should be limited only by the spirit and scope of the following claims.

What is claimed is:

1. A method for authenticating dispensed medications comprising the steps of:
   providing an outside authenticator on a blister pack over at least one dose of medication;
   providing an inside authenticator located inside the at least one dose of medication of the blister pack, wherein the inside authenticator is not completely viewable until the blister pack is opened;
   associating the outside and inside authenticators of each blister pack with each does of mediation in a database;
   providing an authenticating communication system configured to receive scanned information from the outside or inside authenticator from an end user utilizing a third-party scanning tool;
   requesting by the authentication communication system permission to associate a user profile account associated with the end user with the scanning event and,
   whereupon granting permission to associate the user profile of the end user with the scanning event, a secure two-way communication connection is established between the end user and the authentication communication system.

2. The method for authenticating dispensed medications of claim 1, wherein the end user can request and receive medication prescription and adherence information associated with each dose.

3. The method for authenticating dispensed medications of claim 2, wherein the medication adherence information can include any of the following: time since last dose, time until next dose, time to renew prescription, number of doses remaining, and reminder notifications associated with future doses.

4. The method for authenticating dispensed medications of claim 1, wherein the end user can invite medical professional or support person via the authentication communication system to view medication adherence information associated with one or more prescriptions associated with the user profile and compliance information associated with one or more prescriptions.

5. The method for authenticating dispensed medications of claim 4, further including establishing two-way communication connection via the authentication communication system between the end user and the invited medical professional or support person.

6. The method for authenticating dispensed medications of claim 2, wherein the request and receive medication prescription and adherence information step further comprises entering the pharmacy phone number and the pharmacy unique prescription number, wherein the entering step can be performed by scanning the pharmacy label or manually typing the information into the authentication communication system.

7. A method for authenticating dispensed medications comprising the steps of:
   providing an outside authenticator on a blister pack over at least one dose of medication;
   providing an inside authenticator located inside the at least one dose of medication of the blister pack, wherein the inside authenticator is not completely viewable until the blister pack is opened;
   associating the outside and inside authenticators of each blister pack with each dose of medication in a database;
   providing an authenticating communication system configured to receive scanned information from the outside or inside authenticator from an end user utilizing a third-party scanning tool; and
   wherein the authentication communication system is comprised of one or more processors associated with a set of computer executable instructions in memory configured to received scanned information and location information associated with the outside and inside authenticator associated with each dose, utilize the database comprising stored information about outside and inside authenticators associated with each dose for authentication determinations, generate and store user profile information associated with a plurality of end users in a user profile database, and create secure connections between end users and medical professionals or support persons.

* * * * *